United States Patent
Berrang et al.

(10) Patent No.: US 6,374,143 B1
(45) Date of Patent: Apr. 16, 2002

(54) MODIOLAR HUGGING ELECTRODE ARRAY

(75) Inventors: Peter G. Berrang; Henry V. Bluger; Henryk Klosowski; Alan J. Lupin, all of Victoria (CA)

(73) Assignee: Epic Biosonics, Inc., Victoria, B.C. (CA)

( * ) Notice: Subject to any disclaimer, the term of this patent is extended or adjusted under 35 U.S.C. 154(b) by 0 days.

(21) Appl. No.: 09/376,918

(22) Filed: Aug. 18, 1999

(51) Int. Cl.[7] .................................................. A61N 1/05
(52) U.S. Cl. ........................ 607/137; 607/56; 600/379; 600/393
(58) Field of Search ................................ 607/116, 118, 607/137, 55–57; 600/379, 393

(56) References Cited

U.S. PATENT DOCUMENTS

| | | |
|---|---|---|
| 4,261,372 A | 4/1981 | Hansen et al. |
| 4,284,085 A | 8/1981 | Hansen et al. |
| 4,357,497 A | 11/1982 | Hochmair et al. |
| 4,400,590 A | 8/1983 | Michelson |
| 4,419,995 A | 12/1983 | Hochmair et al. |
| 4,532,930 A | 8/1985 | Crosby et al. |
| 4,686,765 A | 8/1987 | Byers et al. |
| 4,762,135 A | 8/1988 | van der Puije et al. |
| 4,819,647 A | 4/1989 | Byers et al. |
| 4,832,051 A | 5/1989 | Jarvik et al. |
| 4,961,434 A | 10/1990 | Stypulkowski |
| 5,037,497 A | 8/1991 | Stypulkowski |
| 5,061,282 A | 10/1991 | Jacobs |
| 5,123,422 A | 6/1992 | Charvin |
| 5,545,219 A | 8/1996 | Kuzma |
| 5,578,084 A | 11/1996 | Kumza et al. |
| 5,645,585 A | 7/1997 | Kuzma |
| 5,649,970 A * | 7/1997 | Loeb et al. .................. 607/57 |
| 5,653,742 A | 8/1997 | Parker et al. |
| 5,800,500 A | 9/1998 | Spelman et al. |
| 6,070,105 A * | 5/2000 | Kuzma ........................ 607/137 |
| 6,074,422 A * | 6/2000 | Berrange et al. ............. 623/10 |
| 6,112,124 A * | 8/2000 | Loeb ........................... 607/137 |

OTHER PUBLICATIONS

The Cochlear Implant, T.J. Balkany, The Otolaryngologic Clinics of North America, vol. 19, No. 2, May 1986.
Cochlear Prostheses, G.M. Clark et al., Churchill Livingstone, New York, 1990, Ch. 1, pp. 1–14.
Dimensions of the Scala Timpani in the Human and Cat with Reference to Cochlear Implants, S. Hatsushika, The Annals of Otology, Rhinology, and Laryngology, 99: 1990, pp 871–876.
A Tantalum–on–Sapphire Microelectrode Array, G.A. May et al., IEEE Transactions on Electron Devices, vol. ED–26, No. 12, Dec. 1979, pp 1932–1939.

(List continued on next page.)

*Primary Examiner*—Kennedy Schaetzle
(74) *Attorney, Agent, or Firm*—Gotlieb, Rackman & Reisman, P.C.

(57) ABSTRACT

A multi-bipolar configured electrode array and means to uniquely position said array within the scalae of the human cochlea is described. Said array is inserted into the scala tympani, scala vestibuli or both, by a surgeon. The electrode array may be pre-formed to lightly hug the modiolar wall of a scala so as to position the electrodes in close proximity to the cochlear spiral lamina and spiral ganglia in the modiolus. Mechanical features within said array allow the surgeon to further position said array against the modiolar wall of the scala, post insertion, and to mechanically retain such positioning of said array. Such positioning is in close proximity to surviving neural sites in the spiral lamina and/or spiral ganglion cells in the modiolus to efficiently stimulate functioning auditory neural elements. The multi-bipolar electrode configuration achieves a high degree of spatial selectivity, thus improving the implantee's speech percepts.

45 Claims, 27 Drawing Sheets

OTHER PUBLICATIONS

A prototype flexible microelectrode array for implant–prosthesis applications, M. Sonn et al., Medical and Biological Engineering, Nov. 1974, pp 778–790.

Spatial Selectivity in a Rotationally Symmetric Model of the Electrically Stimulated Cochlea, Frijns, J.H.M. et.al., Hearing Research, 95 (1996), 33–48).

Photolithographic Fabrication and Physiological Performance of Microelectrode Arrays for Neural Stimulation, H. D. Mercer, et. al., IEEE Transaction on Biomedical Engineering, vol. BME–25. No. 6, Nov. 1978.

An Artificial Cochlea for the Sensory Deaf, M. Sonn, A Raytheon Company Publication PB–219 466, available from the U.s. National Information Service, U.S. Department of Commerce.

A Multiple–Electrode Array for a Cochlear Implant, G. M. Clark, et. al., J. of Laryngology and Otology, vol. XC, No. 7, 1976.

Electroetching of Platinum in the Titanium–Platinum–Gold Metallization on Silicon Integrated Circuits, R.P. Frankenthal, et. al., Journal of Electrochemical Society, 703(123), 1976.

Current Problems in Electrode Development, Brummer et. al., IEEE Trans. Biomed. Eng. vol. BME–25, No. 5, Sep. 1977.

Cylindrical Cochlear Electrode Array for use in Humans, van der Puije, et al., Annals of Otol., Rhino & Laryn, V.98(6), Jun. 1989.

Abstract Proceedings from the 1997 Conference on Implantable Auditory Prostheses, Pacific Grove, California, Aug. 17–21, 1997.

The Scala Vestibuli for Cochlear Implantation—An Anatomic Study, A.J. Gulya et al., Arch. Otolaryngol. Head Neck Surg., vol. 122, Feb. 1996, pp 130–132.

Cochlear Pathology in Presbycusis, H.F. Schuknecht and M.R. Gacek, The Annals of Otology, Rhinology, and Laryngology, 102:1993, pp 1–15.

Cochlear Implants, W.F. House, The Annals of Otology, Rhinology, and Laryngology, 85: 1976, pp. 3–6.

Four Years of Experience with Cochlear Prostheses, I.J. Hochmair–Desoyer et al., Medical Progress through Technology, 8, 107–119 (1981).

Proceedings of the Third European Symposium on Pediattic Cochlear Implantation, The American Journal of Otology, 18(6), Nov. 1997 Supp.

Computer–Aided Three–Dimensional Reconstruction: A Method of Measuring Temporal Bone Structures Including the Length of the Cochlea, A. Takagi and I. Sando, The Annals of Otology, Rhinology, and Laryngology, 98: 1989, pp. 515–522.

Prothèse Auditive par Excitation Electrique à Distance du Nerf Sensoriel à l'Aide d'un Bobinage Inclus à Demeure, A Djuorno and C. Eyries, La Presse Médicale, 1957, 65, No. 63.

Implantation of Multiple Intrcochlear Electrodes for Rehabilitation of Total Deafness: Preliminary Report, C.H. Chouard and P. MacLeod.

* cited by examiner ical implantation, time of implantation since deafness, duration

MODIOLAR HUGGING ELECTRODE ARRAY

CROSS-REFERENCE TO RELATED APPLICATIONS

"Not Applicable"

STATEMENT REGARDING FEDERALLY SPONSORED RESEARCH OR DEVELOPMENT

"Not Applicable"

REFERENCE TO A MICROFICHE APPENDIX

"Not Applicable"

BACKGROUND OF THE INVENTION

This invention relates generally to human hearing, and more specifically to the design and positioning of an electrode array for a cochlear prosthesis.

Human deafness results from numerous factors including trauma, ear infections, congenital factors, ototoxic effects of some antibiotics, and from diseases such as meningitis. Sensorineural damage (damage to the hair cells in the cochlea) is the largest single form of hearing loss. In a healthy ear these hair cells convert acoustic signals in the inner ear to electrical signals that can be interpreted by the brain as sound. It is estimated that over 7% of the U.S. population is affected by sensorineural deafness, and one in a thousand infants is born totally deaf. Extrapolating these percentage figures, it is estimated that there are 30 million people in the world who are profoundly deaf.

Considerable research over the past several decades has been directed towards developing a means to bypass the non-functioning hair cells in the inner ear (or cochlea) by using electrodes to directly stimulate auditory afferent neurons within the cochlea. This so called cochlear implant technology has progressed from early methods of attaching one or more single wire electrodes onto the promontory or the bony shell of the cochlea, to drilling directly into the cochlea, and inserting electrodes into the scalae therein. Electrodes used in modern cochlear prostheses generally use a longitudinal bipolar (or monopolar) electrode configuration where small platinum/iridium balls or circular platinum rings connected internally by thin wires, with the electrodes and wires held together in a smooth elongated silicone carrier, are surgically implanted into the scala tympani (one of the canals within the cochlea), via a hole made in the mastoid bone behind the ear. Entry into the scala tympani is generally via the round window membrane. The electrodes are electrically connected to an electronics package anchored in a cavity made in the mastoid bone. Information is sent to this internal (subcutaneous) electronics package, via RF transmission across the skin barrier, from an external body-mounted electronics package that houses the speech processor, control electronics and power supply.

Such cochlear prostheses are commercially available from a number of companies worldwide, for example, from Cochlear Limited, Sydney, Australia; Advanced Bionics Corporation, Sylmar, Calif., U.S.A.; Med-El Medical Electronics, Innsbruck, Austria; PHILIPS-Antwerp Bionic Systems N.V./S.A., Edegem, Belgium; and MXM Medical Technologies, Vallauris, France.

The surgery time and surgical complexity of implanting these commercial cochlear prostheses is significant, especially for very young and for old persons. The implant procedure usually involves exposure of the mastoid cortex of the implanted ear via elevation of a postauricular skin flap, generally requiring 2.5–4 hours with the patient totally anesthetized, and with the inherent medical risks of total anesthetic. The cost of currently available cochlear prostheses is high, limiting the availability of this technology mostly to the wealthy industrialized countries. A comprehensive introduction to the development of cochlear implants is given in, for example, "Cochlear Prostheses," edited by G. M. Clark, Y. C. Tong and J. F. Patrick, distributed in the U.S.A. by Churchill Livingstone Inc., New York, N.Y. 1990 (ISBN 0-443-03582-2), and in "The Cochlear Implant," (ISSN 0030- 6665) by T. J. Balkany, editor of The Otolaryngologic Clinics of North America, Vol. 19, No. May, 2, 1986. Additionally, some of the early cochlear implant work is described in U.S. Pat. Nos. 4,357, 497; 4,419,995 and 4,532,930.

In spite of the surgical risks, complexity and device costs, currently available cochlear prostheses do provide a major improvement over the alternative—total silence. However, there are still great differences in hearing percepts amongst implanted patients. Some patients after implantation are able to use the telephone, while others can only perceive environmental sounds. Also, there is the great inconvenience, and social stigma, especially for children, in needing to wear an external head-mounted device, connected to a body-worn (or a recently available ear-mounted) electronics package. A totally implanted cochlear prosthesis does not yet exist.

Researchers have tried for many years to ascertain the reasons for the variable hearing results obtained by cochlear implant patients. The consensus of scientific opinion is that the location of the electrodes in the cochlea, age of implantation, time of implantation since deafness, duration of implant use, knowledge of language prior to implantation, duration and intensity of rehabilitation, and patient ability and desire to learn are key factors in determining speech understanding by the implantee. Other factors include the number of functional peripheral neural processes in the basilar membrane and cochlea spiral lamina and/or surviving spiral ganglion cells in the modiolus, the type of speech coding strategy used, and the extent of trauma from surgery during implantation.

The electrode array design parameters are important. For example, the number of electrodes and the spacing between electrodes, the position of electrodes in the scala tympani (or scala vestibuli) with respect to the stimulatable neural sites, and the orientation of the electric field generated between electrode pairs are all factors affecting patient speech percepts.

In spite of all of the potential factors contributing to hearing results, it is clear that the functionality of a cochlear prosthesis will always be limited by the intrinsic design and positioning of the electrode array within a scala. Interestingly, the simple tapered longitudinal bipolar and monopolar electrode arrays using small platinum/iridium balls or circular rings that are now widely used commercially were developed over a decade ago, and were largely based on the relative ease of fabrication and the practicality of surgical insertability, rather than on critical design parameters necessary to achieve optimum neural stimulation.

The use of the simple longitudinal multi ring electrode design, where the rings are held in place with a silicone carrier, has the advantage of simplicity and does not require rotational orientation within the scala. This design is now commonly used by most commercial manufacturers of cochlear implants. However, the longitudinal electrode configuration not only creates an unwanted bimodal distribution of exited nerve fibers (Frijns, J. H. M. et.al., Hearing Research, 95 (1996), 33–48) but only a small segment of the annulus-shaped electric field generated between electrode ring pairs stimulates nerve fibers, thereby wasting a large amount of electrical energy. Frijns, et. al. also suggest that the efficacy of neural stimulation is enhanced when the electric field lines are parallel to the nerve cells rather than perpendicular as is dictated by the longitudinal configuration. Additionally, electrical cross-talk between adjacent ring electrodes becomes an increasing problem as more electrodes are used to obtain better spatial selectivity along the length of the scala.

The small diameter discrete electrode (ie. platinum/iridium ball) type designs have the distinct problem of rotationally twisting during insertion of the array, resulting in some or all of the electrodes facing away from the stimulatable neural sites. Accordingly, designs have been proposed whereby the array preferentially bends in one plane, while maintaining rigidity in the other plane. For example, Charvin, in U.S. Pat. No. 5,123,422, teaches the use of internal hinges or slits, where such hinges or slits are oriented to give flexibility in only one plane, and can be inserted in the scala tympani without curling, thus orienting the electrode sites "to obtain good stimulation of the nerve cells". Hansen, in U.S. Pat. No. 4,261,372, uses "V" shaped notches along one side of the array to permit the array to assume the required curved shape within the scala, and to obtain greater insertion depth of the electrodes by first inserting one part of the electrode into the first turn of the scala tympani and then inserting the other part into the second turn of the scala tympani. Jarvik, et. al., in U.S. Pat. No. 4,832,051, describe an electrode device where "the elements are resiliently attached together so that the stack of elements is stiff in compression along the common axis and is flexible in tension."

None of the above patents, however, addresses the additional critical issue of positioning the electrodes in close proximity to the peripheral processes in the spiral lamina or the spiral ganglion cells in the modiolus. To achieve such proximity requires the electrodes to be positioned snug against the modiolar wall of the scala. To address this proximity requirement, a myriad of electrode array designs have been suggested. For example, Hansen, et. al., in U.S. Pat. No. 4,284,085, use an electrode with two conditions of curvature, where one curvature is temporary, and the other is permanent. The temporary curvature allows insertion with minimum surgical trauma, and by means of a detachable connection, the array assumes a position to obtain an optimum final position relative to the acoustic nerves over the entire electrode length. Michelson, in U.S. Pat. No. 4,400,590, teaches a multichannel electrode array comprised of discrete bipolar radially positioned electrode pairs on one side of the array, where such array is positioned to "be located adjacent predetermined auditory nerve endings in the basilar membrane", a location that seems, in hindsight, not an optimum location for neural stimulation as the nerve fibers in this locale are unmyelinated and thus difficult to stimulate. A design by Jacobs, in U.S. Pat. No. 5,061,282, similarly tries to stimulate neurons connected to auditory nerves in the basilar membrane using a plurality of transducer elements disposed along the length of the cochlea adjacent to the basilar membrane. Byers, et. al., in U.S. Pat. No. 4,819,647, describe a multichannel array where the electrode conductors have elongated cross-sections which are aligned to allow the array to readily flex in the plane defined by the array spiral, limiting flexing in the vertical direction, with the overall array having spiral shape corresponding generally to the shape of the scala tympani. The micro ball-shaped electrodes are positioned at right angles with respect to each other, and displaced longitudinally from one another, where one electrode is positioned facing the basilar membrane and the other facing the modiolus. Stypulkowski, in U.S. Pat. Nos. 4,961,434; 5,00,194 and 5,037,497, describes a number of designs for a cylindrical or tapered cylinder flexible array with various flush and recessed electrode surfaces in a radial bipolar configuration, with details of fabrication methods for such devices. However, these designs do not allow for either rotational positioning within the scala tympani to orient the electrodes nor do they allow for overall positioning of the array near the modiolus or spiral lamina. Kuzma, in U.S. Pat. Nos. 5,545,219 and 5,645,585, illustrates a flexible electrode carrier connected to a flexible positioning member used to force the electrode carrier into a close modiolus-hugging arrangement and for disposing the electrode surfaces towards the spiral ganglion cells in the modiolus. In a further patent (U.S. Pat. No. 5,578,084) Kuzma, et. al., disclose an electrode array design whereby one part of the array material slowly absorbs water from the surrounding cochlear perilymph fluid, thereby expanding the array to engage the electrodes to the modiolar (or inner) wall of the canal. In another version of this concept, Kuzma et. al., in U.S. Pat. No. 5,653,742, further disclose an electrode carrier that is either pre-formed and held with a bioresorbable stiffening element which dissolves in the cochlear fluid after implantation, or contains biasing fins held folded against the carrier which can flex outward upon dissolution of the holding sheath, such that the fins or pre-curved shape of the array act to position the array towards the modiolar wall. Spelman et. al. in U.S. Pat. No. 5,800,500, teach an electrode design comprised of a plurality of insulated wires wrapped around a tube containing a memory shape wire, where selected areas of wire insulation are removed with a laser, both longitudinally along the length of the array and laterally along the array circumference. The memory shape wire (or polymer) acts to position the array towards the modiolar wall upon reaching body temperature.

The electrode array devices that have been disclosed suffer from a variety of limitations which predispose them to meeting some criteria while not meeting others. The electrode array criteria that appear to provide for optimum performance are:

(a) electrode proximity to spiral ganglion cells in the modiolus and the peripheral processes in the spiral lamina, (b) optimal orientation of the electric fields generated by paired electrodes, (c) a high density of electrodes (electrodes per unit length) without significant signal cross-talk between electrode pairs and (d) surgical insertability of the electrode array into the entire length of the scala, generally the scala tympani, especially to the apical end.

Since nerve fibers stimulated with an electric field parallel to said nerve fibers have a lower stimulation threshold, an optimum electrode orientation would be radially bipolar. However, it is essential that the electrodes be positioned as close as possible to the stimulatable nerve fibers so as to minimize threshold currents. Anatomically, there appear to be two distinct locations, one near the modiolus to stimulate the spiral ganglion cells, and one near the spiral lamina to stimulate the peripheral processes therein. However, these two stimulation sites are orthogonal one to the other, thus requiring an orthogonal electrode design to accommodate both stimulatable sites. Interestingly, stimulation near the basilar membrane would require high currents, since the fibers therein are unmyelinated, with fiber myelination starting near the habenula perforate. Since the electrodes used in the invention can be positioned close to the spiral lamina, it is possible to achieve high spatial selectivity and high electrode density, although such stimulation must be done shortly after onset of deafness since the peripheral processes in the spiral lamina tend to atrophy relatively quickly if not stimulated. Stimulation of the spiral ganglion cells in the modiolus requires the electric field to extend further into the nerve bundle, although this increases the probability of ectopic stimulation (or stimulation of fibers in scalae turns not containing the stimulating electrode). This aspect may be somewhat alleviated by using an electrode array which hugs the modiolar wall in each of the scala tympani and scala vestibule.

Surgical insertability of the array is critical. However, the array stiffness requirements are contradictory. Said array must be sufficiently stiff to be insertable, especially to traverse the sharp bends in the scala tympani between the round window and the first turn, yet be highly flexible so as to avoid damaging the delicate structures within the cochlea. Accordingly, most conventional devices use a soft, flexible medical grade silicone carrier, which is difficult to fully insert, and some cochlear implant manufacturers provide specialized insertion tools to assist in the insertion of their electrode arrays. The invention addresses this issue through the use of a simple microformed polyfluorocarbon carrier attached to lithographically created electrodes and conductors (embedded in a polyfluorocarbon film), where such an array can be conveniently and safely inserted into the scala tympani by a surgeon.

Ease of fabrication of the electrode array is also essential. Most conventional arrays rely on manual fabrication techniques that lack process control. The lithographic technique used in this invention facilitates low cost non-manual fabrication which allows for greater process control and consequently greater reliability of the frnished product. This technique also allows for higher conductor wire density than can be achieved with conventional fabrication techniques. The object of this invention is to provide an implant that overcomes the limitations of the prior art, as well as to provide an improved method of surgical positioning of such a device.

BRIEF SUMMARY OF THE INVENTION

The invention comprises an electrode array containing three main components, namely:
(a) a bio-inert film holding conductor lines and at least two radial bipolar oriented electrodes, and
(b) a bio-inert carrier with an opening or hole substantially through the center of the longitudinal axis of the carrier, and, in a further embodiment, with at least one partially circumferential notch (or "V" groove) disposed along the longitudinal axis of the carrier, and
(c) a beading designed to slide smoothly within the longitudinal opening or hole in the carrier The film, carrier and beading are preferentially fabricated from a flexible biocompatible material, such as the polyfluorocarbon FEP, where said carrier has, on opposing sides, one rounded surface and one substantially flat surface, and a lumen-like opening substantially through the center of the longitudinal axis of the carrier. The carrier serves as a substrate to provide a physical structure to support the electrodes and conductor lines embedded in a thin polyfluorocarbon film, where said film is heat bonded to the carrier. The insertion of a beading into the lumen-like hole in the carrier allows the surgeon to control the shape of the carrier by pushing or pulling on the beading which is preferentially attached to the apical end of the carrier. Partially circumferential notches (or "V" grooves) in the combined film/carrier assembly provide flexibility for insertion of the array into one of the scala of the cochlea and for controlling flexure to conform to the conical helix shape of the scala. In the preferred embodiment, said partially circumferential notches are disposed ad-modiolar (ie. on the inside of the conical helix or spiral shaped array). In an alternate embodiment, said notches are disposed ex-modiolar (ie. on the outside of the conical helix or spiral shaped array). Said notches are preferentially disposed along the longitudinal axis of the film-carrier assembly such that one or more of said notches are disposed between each group of bipolar radial electrodes. In still a further embodiment, said notches are disposed between every second, third or more groups of bipolar radial electrodes.

In two additional embodiments of the invention, the electrode array is comprised of either:
(a) a bio-inert film holding conductor lines and at least two radial bipolar oriented electrodes, or
(b) a bio-inert film, holding conductor lines and at least two radial bipolar oriented electrodes, and a bio-inert carrier, with at least one partially circumferential notch (or "V" groove) disposed along the longitudinal axis of the carrier.

Those skilled in the art will appreciate that the film, carrier and beading can be made from, for example, any one of the various polyfluorocarbons, polyethylene, polypropylene polyimide, polyamide or other bio-inert organic polymers.

The combined film-carrier-beading structure (or alternatively the film structure, or the film/carrier structure) containing the film-embedded electrodes and conductors (referred to hereinafter as the electrode array or array) is preferentially shaped into a three-dimensional conical helix, (referred to hereinafter as the conical helix) substantially conforming to the three-dimensional conical helix shape of the scala modiolar wall. The said array has one conical helix configuration to fit the scalae of the right ear and a mirror image conical helix configuration to fit the scalae of the left ear. In this document, the term diameter, when it refers to the conical helix or to the spiral shape of the electrode array, describes the decreasing diameter of the conical helix or spiral from the basal end to the apical end of said array.

In an alternate embodiment, the array can be shaped into a two-dimensional spiral. In a further embodiment, the array can be left substantially straight (or non pre-shaped) for insertion into a scala. Formation of the array into a conical helix or spiral shape is accomplished by heating said array to near the melting or softening point, and holding said array at approximately such temperature for sufficient time to allow the material to substantially retain said conical helix or spiral shape upon cooling. The array is thus "normalized" (ie. the permanent change from one shape to another shape via heating and subsequent cooling back to ambient temperature) substantially retaining said conical helix or spiral shape at room or body temperature. An additional embodiment of the invention is to create a conical helix or spiral shape that is up to 50% smaller in diameter than the diameter of the conical helix shape of the human scalae modiolar wall so as to position the array to "hug" the modiolar wall upon insertion. In another embodiment, the beading is "normalized" while the film-carrier assembly is not, such that the beading serves to induce curvature of said film-carrier assembly upon insertion into the cochlear scala.

For the preferred embodiment, the beading is made of the polyfluorocarbon FEP, a bio-inert polymer. For the preferred embodiment, the beading and the hole both have substantially rectangular cross-sectional shapes, where the longer dimension of the rectangle is parallel to the flat portion of the cross-section of the carrier. The rectangular shaped polymer beading is designed to slide smoothly within the carrier hole, where the orientation of the rectangular beading now serves to assist with preferential curving of the electrodes on the carrier towards the scala modiolar wall. In alternate embodiments, the cross-sectional dimension of the beading may be substantially smaller than the cross-sectional dimension of the hole, wherein said beading slides smoothly within the hole in said carrier.

While the preferential longitudinal shape of the carrier is tapered, being larger in cross-section at the basal end and smaller at the apical end, in an alternate embodiment, said carrier has a longitudinal shape that is not tapered, having substantially the same cross-sectional dimension along its entire length. The cross-section of the carrier having ad-modiolar notches has one rounded surface and one substantially flat surface in the preferred embodiment. Another embodiment, includes a substantially oval cross-section for the carrier with ex-modiolar notches. Said carrier, in further embodiments, can have a cross-section that is round, oval, square, rectangular, triangular, or substantially any other shape.

In the preferred embodiment, the longitudinal hole in the carrier extends completely through the length of said carrier from the basal end to the apical end. In another embodiment, said hole extends from the basal end only partially through the length of said carrier.

For the preferred embodiment containing ad-modiolar disposed partially circumferential notches, pushing on the beading also serves to straighten not only the apical end of the carrier but also the entire body of the carrier. For an alternate embodiment, containing ex-modiolar disposed partially circumferential notches, pulling on the beading also serves to straighten not only the apical end of the carrier but also the entire body of the carrier.

For the preferred embodiment, the beading cross-section is substantially the same along the longitudinal length. In an alternate embodiment, the beading cross-section is tapered, being larger at the basal end and smaller at the apical end. In a further embodiment, the beading can alternatively be comprised of a biocompatible wire or memory shape wire (see for example, U.S. Pat. No. 5,800,500 by F. Spelman, et. al.), either bare or inside a flexible tube, where such beading is used to shape the electrode array for surgical insertion and or assist in positioning the electrode array closer to the modiolus. The beading may, or may not, be removed from the array after surgical insertion of the array.

The apical end of the beading is preferentially attached to the carrier apical end, with the external part of the carrier apical end rounded to minimize trauma during insertion, and the carrier basal end attached to an insertion tool. In the preferred embodiment, for the array containing ad-modiolar notches, said tool allows the surgeon to manually move the beading gently inwards (towards the apical end) during insertion into the scala, such movement acting to straighten the highly flexible array tip, and the entire array, preventing said tip from curling over onto itself or puncturing the basilar membrane. In an alternate embodiment, for the array containing ex-modiolar notches, said tool allows the surgeon to manually move the beading gently outwards (away from the apical end) during insertion into the scala, such movement acting to straighten the highly flexible array tip, and the entire array, preventing said tip from curling over onto itself or puncturing the basilar membrane. In a further embodiment, the beading is not attached to the array apical end, and can be removed after insertion, or simply left in the carrier hole.

The use of said insertion tool by the surgeon facilitates array insertion into the scala by conventional entry via elevation of a postauricular skin flap and exposure of the mastoid cortex, or via the auditory canal Upon insertion of the apical end of the electrode array to substantially the location of the cochlear helicotrema, the beading at the basal end may be pulled by the surgeon to snug the array to the modiolar wall, after which the insertion tool is detached from the array. In one embodiment, said beading is then cut near the point of array entry into the bony cochlea. A further embodiment of the invention includes means to tighten and anchor said beading at the basal end post-insertion so as to more tightly and permanently position the array against the modiolar wall. In a further embodiment, the beading is simply removed by the surgeon. Note that the beading serves two key functions:

(a) to allow the conical helix or spiral shaped electrode array to be substantially straightened for convenient surgical insertion of the array into a scala, or into an insertion tool for subsequent insertion into a scala, and (b) to allow the diameter of the conical helix, spiral or straight shaped array to be made smaller post-insertion (thereby more closely hugging the modiolar wall) by pulling (or pushing) on the beading.

In the preferred embodiment, the metal used for both electrodes and conductors is platinum. Other bio-inert metals such as iridium, gold, tantalum, rhodium, rhenium or alloys thereof, and one or more coatings of one metal over the other, may also be used. The metal conductors and radially oriented multi-bipolar metal electrodes can be formed using a variety of standard technologies.

The metal electrodes and metal conductors can be fabricated simultaneously, and subsequently sandwiched between two thin layers of film. Said film layers can be subsequently bonded together, where said films are comprised of a bio-inert organic polymer, and the electrode surfaces subsequently opened to expose the electrode metal surface. The shape of the exposed metal electrode surfaces, in the preferred embodiment, is square. In other embodiments, the shape of said exposed electrode surfaces can be rectangular, round, oval, triangular or substantially any other configuration. The planar film layer is then bonded to the carrier, substantially encapsulating said carrier to create the array structure, with, in one embodiment, the ad-modiolar partially circumferential notches in the array being pre-fonned during molding of the carrier, with one or more notches positioned between groups of multi-bipolar oriented electrodes. "Cut-outs" are preferentially disposed in the film between the groups of electrodes, wherein said "cut-outs" match the notches in the carrier when the film is bonded to the carrier. In another embodiment, said notches in the carrier are mechanically cut out. Said notches allow the surgeon to rotationally orient the array in a scala, preferably the scala tympani, such that the multi-bipolar electrodes are oriented to face towards the modiolus and or spiral lamina.

In an alternative embodiment of the invention, wherein the electrode array is composed solely of a film containing electrodes and conductor lines, said "cut-outs" are preferentially disposed in the film between the groups of electrodes. Upon forming the film into a tube-like conformation, said "cut-outs" allow normalization of the array into a conical helix or spiral, and facilitate rotational stability of the array within the scala upon insertion. In this embodiment, the array can be positioned in the scala such that the "cut-outs" are oriented either admodiolar or exmodiolar.

In still another embodiment of the invention, the film/carrier assembly forms the complete electrode array. In this embodiment, there is no hole down the longitudinal axis of the carrier and there is no beading. Partially circumferential notches are preferentially disposed ad-modiolar and the array is preferentially normalized into a conical helix (or spiral) shape to facilitate positioning of said array to hug the modiolar wall of the scala. An alternate embodiment involves the disposition of the partially circumferential notches in an ex-modiolar location along the length of the carrier. Without the beading, the surgeon has a narrow span of control over the array during insertion, however, the conical helix (or spiral) shape of the array assures that the electrodes are positioned in close proximity to the spiral lamina and the spiral ganglion cells.

To allow for both movement and future head growth in implanted infants and children, the conductor lines between the electrode array and the electronics package contain a series of pleats to allow the device to "stretch" so as to prevent breakage of said conductor lines or spontaneous explantation of the array from the cochlear scala(e).

An alternate embodiment includes array insertion into the scala vestibuli, where the electrodes are oriented to face towards the modiolus. A yet further embodiment is the insertion of arrays into both the scala tympani and the scala vestibuli, such that electric fields between electrode pairs within the same scala, or between scalae, can be configured to have electric field lines substantially parallel to nerve fibers in the spiral lamina and or the spiral ganglia in the modiolus.

For safety reasons, it is essential that the array be surgically removable in case of failure, infection or for any other reason. Since the inventive features of the array do not contain any substantial protruding elements, and since the partially circumferential notches allow convenient flexure of the overall array, explantation of said array is feasible.

Other aspects of the invention will be appreciated by reference to the detailed description of the invention and to the claims.

BRIEF DESCRIPTION OF THE SEVERAL VIEWS OF THE DRAWINGS

The preferred and alternative embodiments of the invention will be described by references to the accompanying drawings, in which.

DETAILED DESCRIPTION OF THE INVENTION AND BEST MODE OF PRACTISING THE INVENTION

Figure 1:
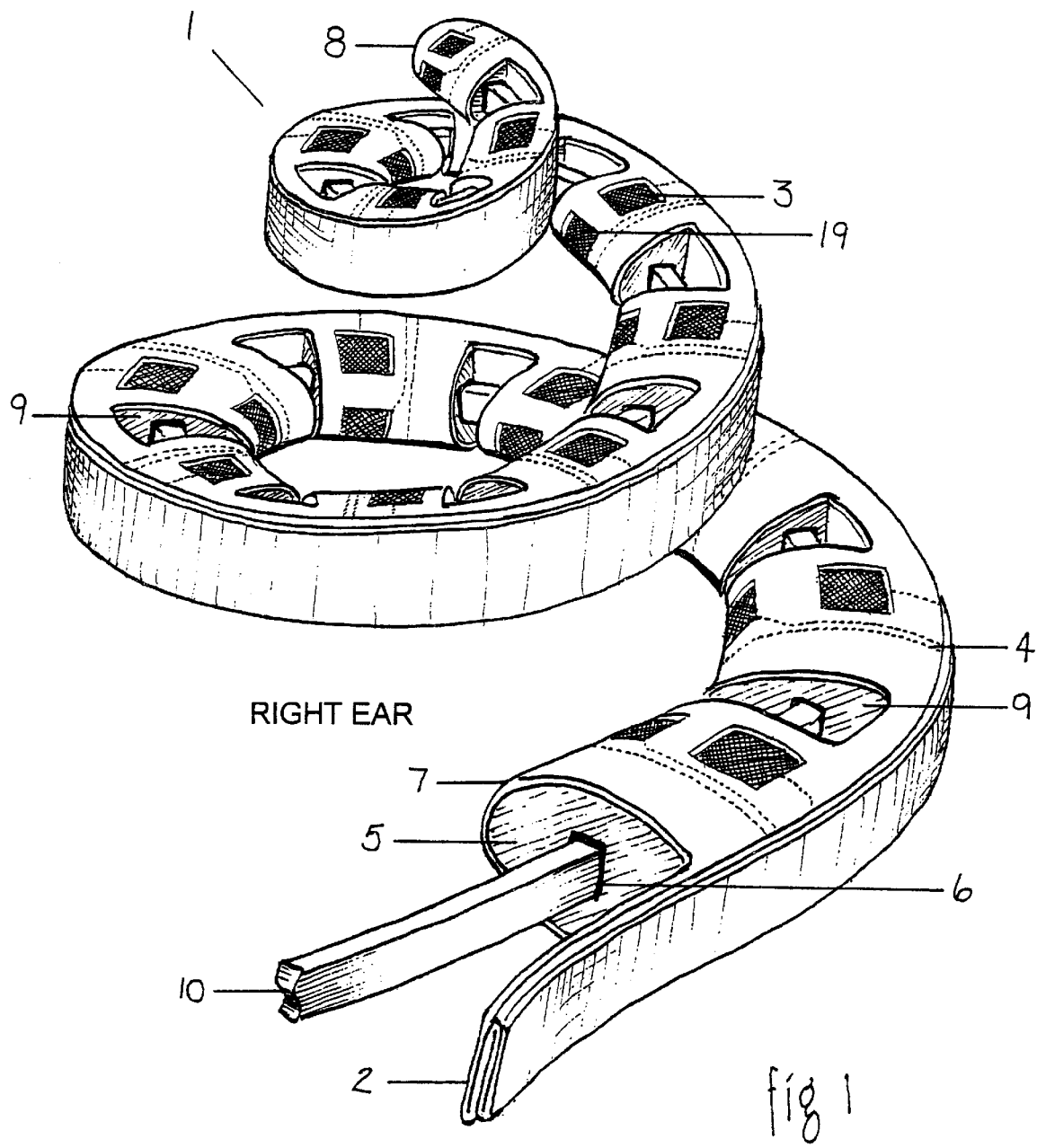
FIG. 1 is perspective view of the preferred embodiment of the invention showing the conical helix-shaped electrode array, with the partially circumferential notches disposed on the ad-modiolar part of the array, for insertion into the right ear.

FIG. 1 illustrates the implant device according to the preferred embodiment of the invention 1, for insertion into the scala tympani of the right ear. The conical helix shaped device is comprised of three components:

(a) a biologically inert and electrically insulating film 2 with metal electrodes 3 and 19 and metal conductors 4 disposed substantially within the film 2, (b) a flexible biologically inert carrier 5, containing a lumen-like tapered hole 6 substantially along the longitudinal axis, said hole being larger at the basal end 7 and smaller at the apical end 8, said carrier also containing various partially circumferential notches 9, ad-modiolar disposed along the array, for enhanced flexibility, and (c) a biologically inert beading 10 designed to slide smoothly within the lumen-like hole 6 within said carrier 5 and attached at the apical end 8 of the carrier. In an alternate embodiment, the beading 10 is not attached to said carrier 5 at any point within the carrier 5. By pushing on said beading 10, the surgeon can straighten the electrode array 1 to assist in the process of insertion of said electrode array 1. In this embodiment, the beading 10 would be anchored substantially near the basal end of the carrier 5, or removed from said carrier 5 following insertion.

The electrodes 3 and 19 can be oriented in groups of two (or alternately in groups of three or four) in a radial bipolar configuration, with a total of one to sixteen (or more) such groups along the length of the array. Such an arrangement allows two or more of the radially bipolar oriented electrodes to effectively stimulate functioning neural auditory peripheral processes by creating an electric field that is substantially parallel to the nerve fibers in either the area of the spiral lamina or the area of the spiral ganglia, or both. For the preferred embodiment, sixteen groups of three radial bipolar oriented electrodes 3 and 19 are disposed along the electrode array 1 in the scala tympani 12 (FIG. 2), shown in a cut-view of the bony cochlea 14, said array 1 having a length of about 10–18 mm, where such length, when substantially positioned against the modiolus 11, enables the array 1 to reach the scala apical end 8 (ie. the helicotrema) to stimulate nerve fibers representing low frequencies, for example 100–300 Hz, to improve speech discrimination by the implantee. For another embodiment, sixteen groups of three radial bipolar oriented electrodes 3 and 19 are disposed along the electrode array 1 in the scala vestibuli 13. In further embodiments, one to sixteen or more groups of electrodes, each containing two or four radially bipolar oriented electrodes, or one electrode, can be disposed along the length of the electrode array, where said array is inserted into the scala tympani 12 or scala vestibuli 13, or both.

The biologically inert, flexible and tapered carrier 5 containing the proximally disposed partially circumferential notches or grooves 9 is preferentially fabricated from the polyfluorocarbon FEP. Other carrier materials include one of the other polyfluorocarbons, polyethylene, polypropylene, silicone, polyamide, polyimide, or other similar polymers. The tapered carrier 5 is about 0.7 mm to 1.2 mm diameter at the basal end, reducing to about 0.3–0.6 mm diameter at the apical end. Those skilled in the art of molding polymers will appreciate that there are various methods for fabricating such small components.

In the preferred embodiment, the lumen-like hole 6 disposed substantially through the longitudinal axis of the carrier 5 is rectangular in cross-section, having the longer side parallel to the flat side of said carrier 5, and tapered, in cross-sectional dimensions from the basal end to the apical end of said carrier 5. In an alternate embodiment, said hole 6 is not tapered, being substantially equal in cross-sectional dimension from the basal end to the apical end of said carrier. In further embodiments, the hole 6 may be substantially round, oval, square, triangular, or any other shape, and said hole 6 may be totally or partially offset from the longitudinal axis of said carrier 5. Said hole 6, in still further embodiments, may be disposed completely through the length of said carrier 5, or only partially through the length of said carrier 5.

Preferentially, the cross-sectional dimension of the carrier 5 is tapered, being substantially narrower at the apical end than at the basal end. In another embodiment, said carrier 5 is not tapered, having substantially the same cross-sectional dimension at the basal end as at the apical end. The cross-section of said carrier 5, in a further embodiment, may be substantially round, oval, square, rectangular, triangular, or any other shape. Additionally, the apical end 8 of the carrier 5 is rounded to further minimize damage to the scala during insertion.

In the preferred embodiment, the beading 10 has substantially the same shape as the hole 6 and is designed to slide smoothly within the carrier 5. The cross-sectional shapes of said beading 10 and said hole 6 may be substantially different from each other (eg. a rectangular hole housing a round beading) in a further embodiment.

The partially circumferential notches 9 allow the carrier to preferentially bend in the direction of the notches. As a result, when force is applied to shorten the carrier, it will bend in the direction of the notches. Such a force may be applied by securing the beading 10 to one end of the carrier and pulling it in outward from the opposite end of the carrier. This allows the surgeon to navigate around obstructions and into the cochlea while the array is being inserted by selectively tugging or releasing the beading. Once the array is in place within the cochlea, a slight tugging on the beading results in inward bending at the notches (when they are disposed ad-modiolar) and therefore causes the array to lightly hug the modiolar wall.

Preferentially, the electrode array 1 has a conical helix shape, designed to substantially follow the natural three-dimensional conical helix shape of the human scala, such as the scala tympani 12 (see for example, S. Hatsushika, et. al., Ann. Otol. Rhinol. Laryngol. 99:871–876, 1990), where the electrode array conical helix shape is disposed to fit against the modiolar wall 15 (ie. towards the modiolus) after insertion into the scala tympani 12. In an alternate embodiment, the electrode array 1 can also be positioned in the scala vestibuli 13 (see FIG. 18). In a further embodiment, the carrier conical helix diameter can also be made the same size, or even somewhat larger, than the diameter of the scala, since it is possible, post-operatively, to engage the electrodes 3 and 19 against the modiolar wall 15 by tightening the beading 10 within the core of the carrier, or, if memory shape material is used, by causing the diameter of the carrier conical helix shape to shrink. In one embodiment, the beading can also be permanently anchored taut post insertion to fix the decreased conical helix diameter and thereby hold the electrodes 3 and 19 against the modiolar wall 15. In another embodiment, the carrier/film assembly (5 and 2) remains straight (not normalized) while the beading 10 is normalized into a conical helix or spiral shape. Curvature of the array 1 is achieved on insertion of said beading 10 into the hole 6 in the carrier.

In alternate embodiments, the electrode array can have other shapes, for example, a two-dimensional spiral shape or a straight shape, which can be made to bend to fit into a scala of the cochlea by manipulation of the beading 10. For said two-dimensional spiral shape, the diameter of the spiral can be made somewhat smaller than the diameter of the modiolar wall 15 such that the array will hug said modiolar wall 15 following insertion. Such a two-dimensional configuration is simpler to fabricate, but does not conform as ideally to the natural three-dimensional conical helix shape of the scalae during insertion or after insertion.

A further embodiment is to have a straight shape when in the relaxed state (ie. not heat treated to "normalize" the shape to a conical helix or spiral), such a device bending to the conical helix shape of the scala upon insertion into the cochlea and movement (slight retraction) of the beading. The surgeon could then anchor the beading so as to position and hold the array substantially against the modiolar wall 15.

It is interesting to note that the size of the cochlea 14 does not change substantially from birth to adulthood. Also, there is surprisingly little size variation in the human cochlea between males and females, between racial groups, and between individuals within a racial group.

Figure 13:
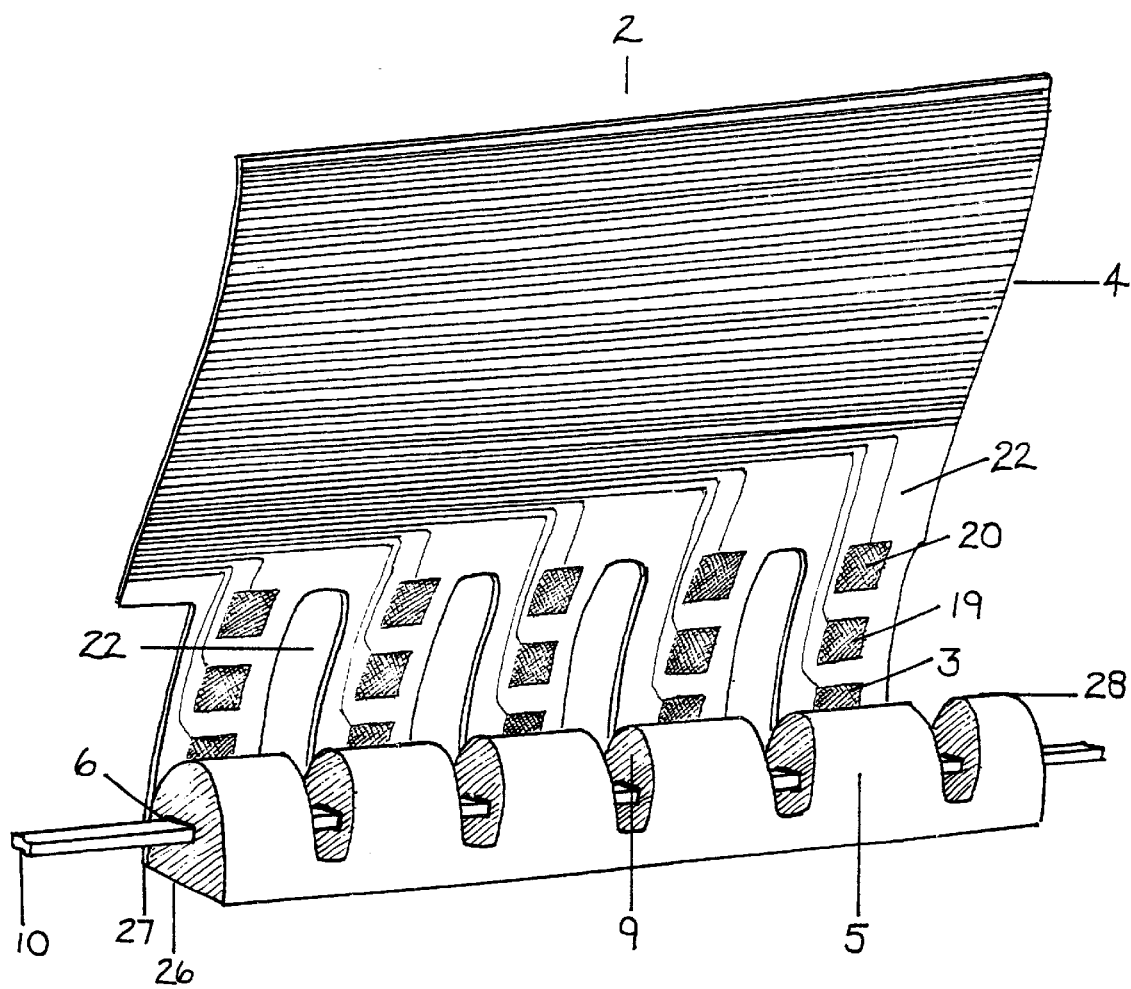
FIG. 13 is a perspective view of the preferred embodiment of the invention showing the film being rolled over the carrier, with the beading disposed within the lumen-like hole of the carrier.

The electrode array 1 can, if comprised of materials such as polyfluorocarbons, be conveniently shaped to have a diameter that is 0–50% smaller, preferentially about 10%, than the diameter of the human cochlea, by heat forming the electrode array 1 into a substantially permanent conical helix (or spiral) configuration. To be able to flex and or maintain the conical helix shape (or a two dimensional spiral) of the electrode array 1 with minimal stress, a series of partially circumferential notches (or "V" grooves) 9 are ad-modiolar disposed along the longitudinal length of the array, where one or more such notches 9 is positioned substantially between each group of radial bipolar electrodes, 3, 19, and 20 (FIG. 13). Electrical contact to the electrodes 3 and 19 is via conductors 4 embedded in a polymer film and folded to form a ribbon cable 2.

In an alternate embodiment of the invention 1, the electrode array is comprised of only two components:
(a) a biologically inert and electrically insulating film 2 with the metal electrodes 3 and 19 and metal conductors disposed substantially within the film 2,
(b) a flexible biologically inert carrier 5 containing various partially circumferential notches 9, ad-modiolar disposed along the array, for enhanced flexibility.

In a further embodiment of this two component invention, the film/carrier assembly is normalized into a spiral shape, suitable for insertion into either the right ear or the left ear. The carrier 5 is preferentially tapered, having a wider diameter at the basal end 7 than at the apical end 8. Another embodiment includes a non-tapered carrier 5. Still a further embodiment involves a carrier 35 (FIG. 20) with partially circumferential notches 33, ex-modiolar disposed along the array.

Figure 2:
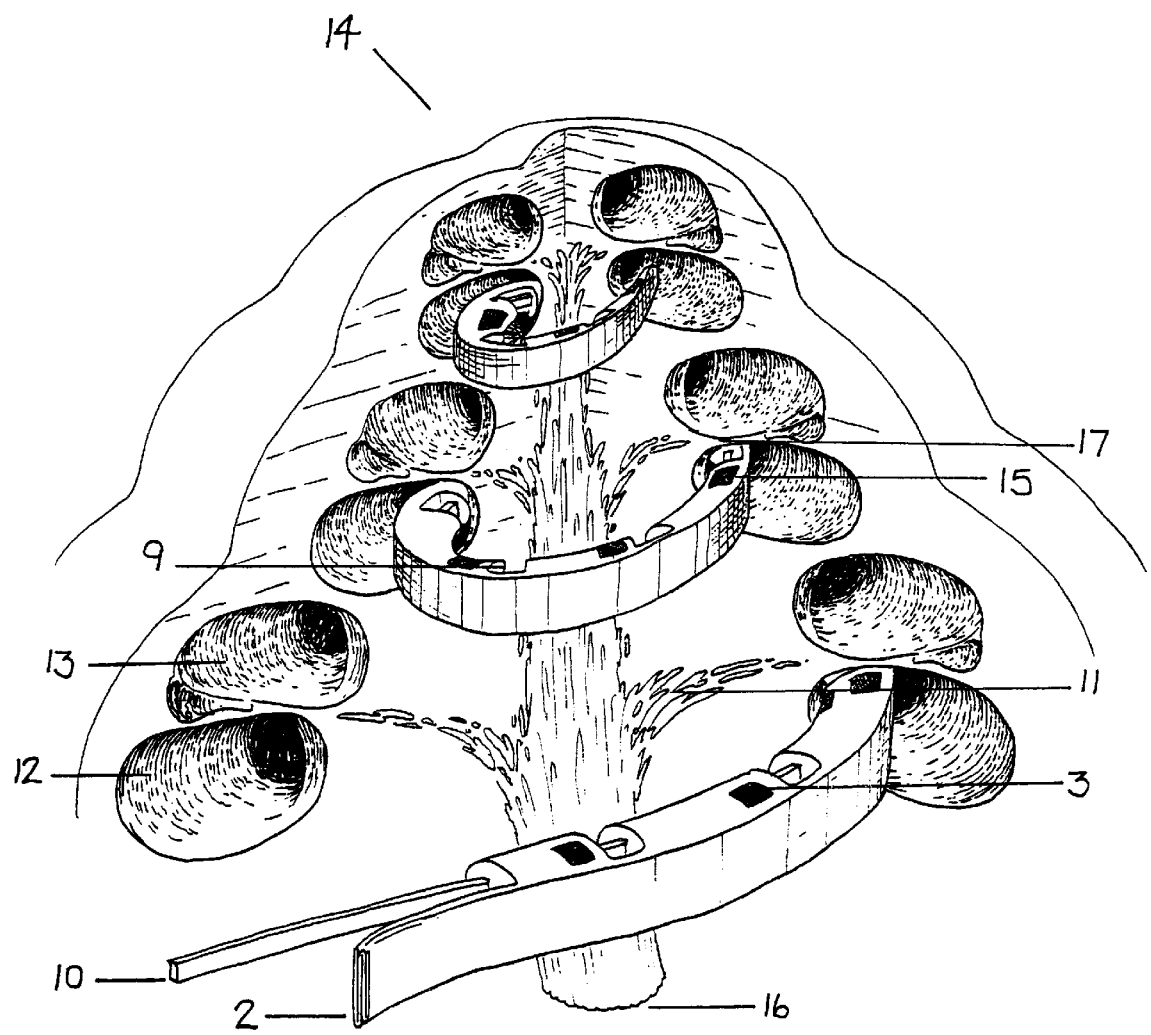
FIG. 2 is an enlarged cutaway, perspective view of the cochlea with the preferred embodiment of the invention in place.

FIG. 2 shows a cutaway, perspective view of the cochlea 14 and cochlear nerve 16 with the preferred embodiment of the invention 1 in place. The carrier has been normalized to a conical helical shape while the beading has not been normalized. The beading has been anchored at the apical end of the carrier prior to insertion of the array into the cochlea. Reissner's membrane 31 (FIG. 16), which separates the scala vestibuli 13 and the scala media 30 should remain intact during insertion of the preferred embodiment of the invention 1 into the scala tympani 12. It is noted that the surface of the electrodes 3 and 19 are positioned to touch or almost touch the modiolar wall 15 to stimulate the spiral ganglia in the modiolus 11 and spiral lamina 17. Said electrode orientation enables the electric field generated between key pairs of electrodes to be in close proximity and substantially parallel to the nerve cells.

Figure 3:
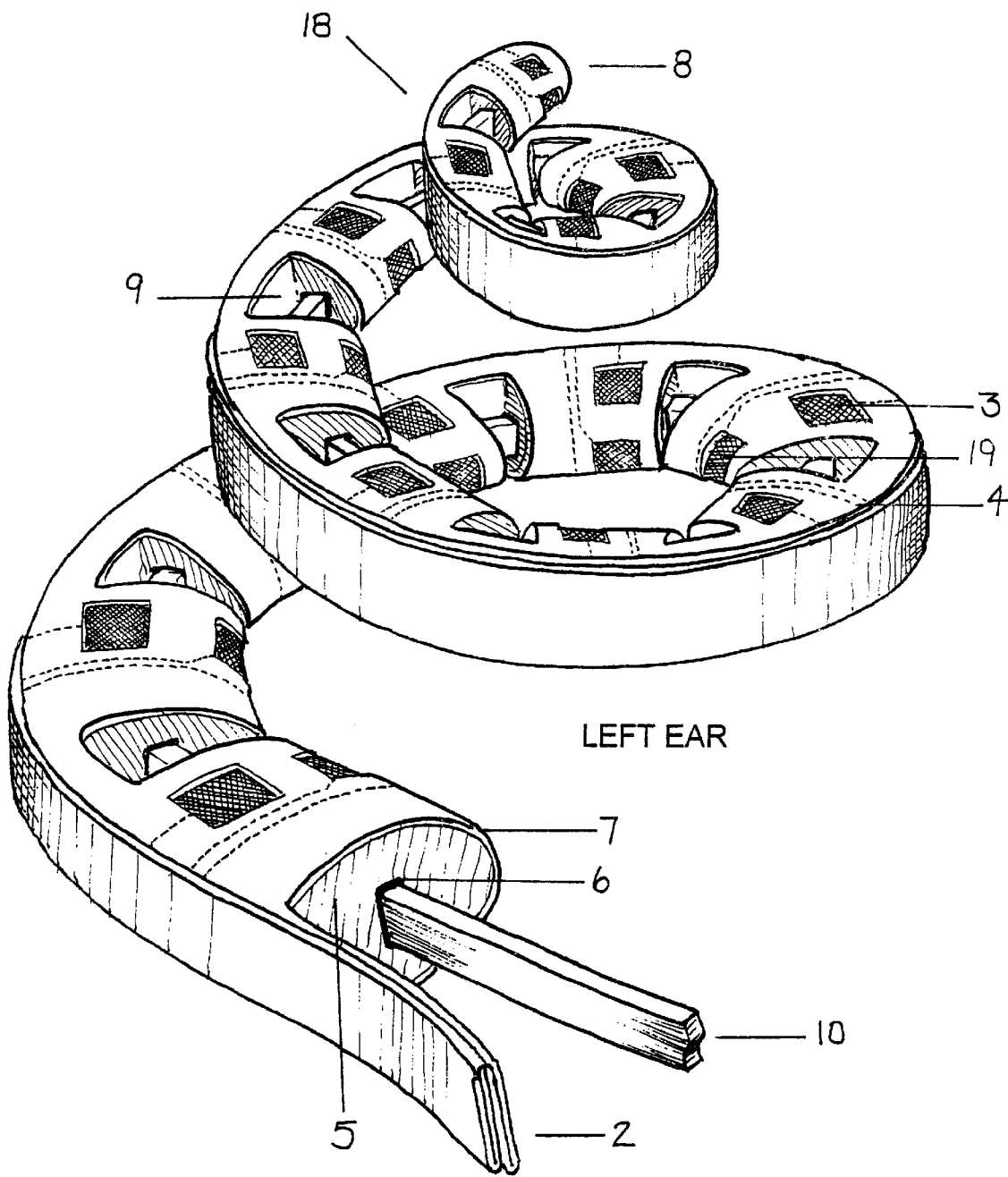
FIG. 3 is a perspective view of the preferred embodiment of the invention showing the conical helix-shaped electrode array, with the partially circumferential notches disposed on the ad-modiolar side of the array, for insertion into the left ear.

FIG. 3 illustrates an implant device according to the preferred embodiment of the invention 18, for insertion into the left ear. (For convenience, all other references to the invention are shown for the right ear, except FIG. 3, which illustrates the configuration for the left ear.) The design and features of said left ear embodiment of the invention 18 is the same as that described for FIG. 2, except that the three-dimensional conical helix shape 18 for the left ear is a mirror image of that shown in FIG. 2. By implication, all references, descriptions and embodiments for the three-dimensional conical helix shape of the right ear apply to the version for the left ear.

Figure 4:
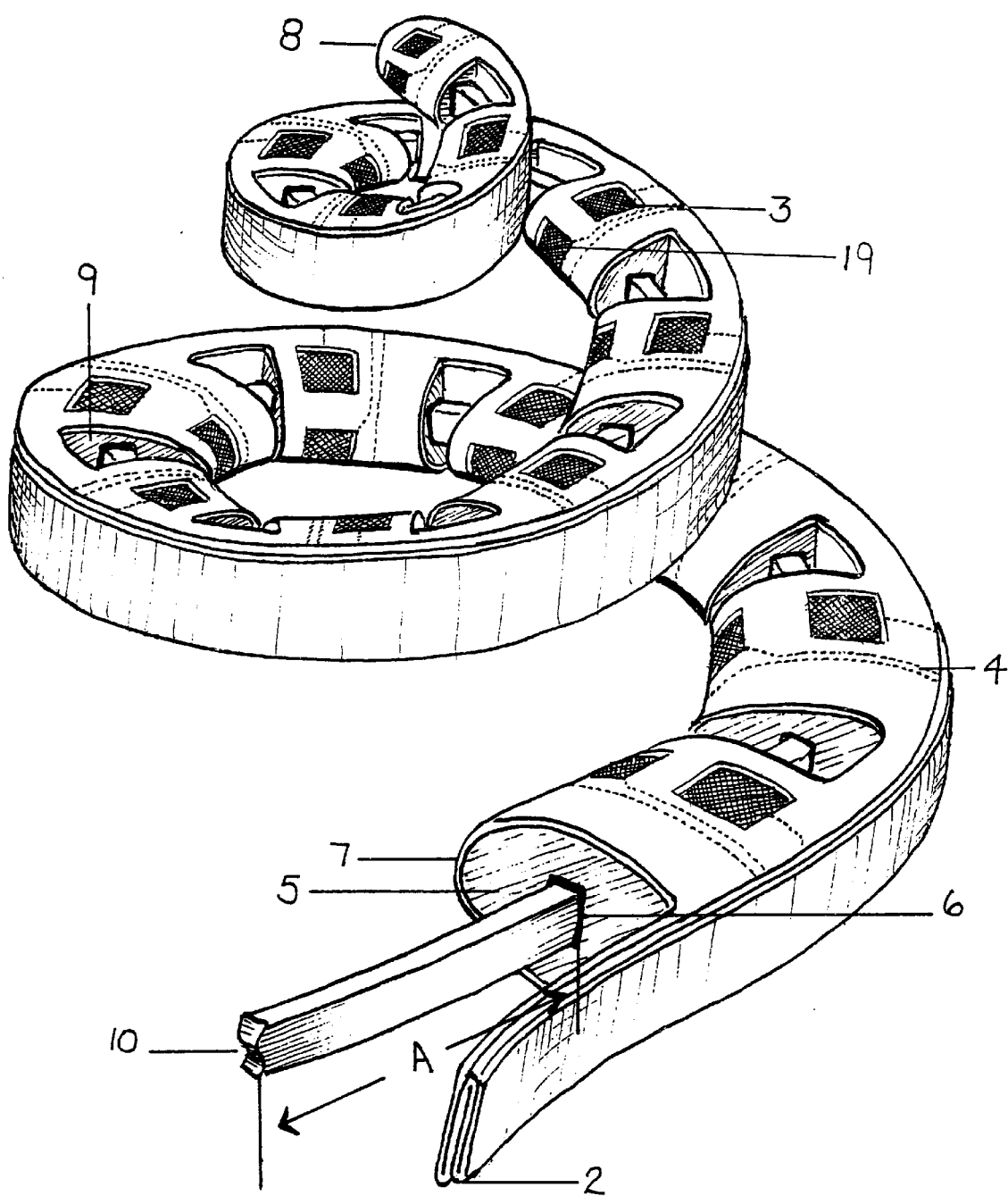
FIG. 4 is a perspective view of the preferred embodiment of the invention showing the relaxed state of the conical helix-shaped electrode array, with the partially circumferential notches ad-modiolar disposed, for insertion into the right ear.
Figure 5:
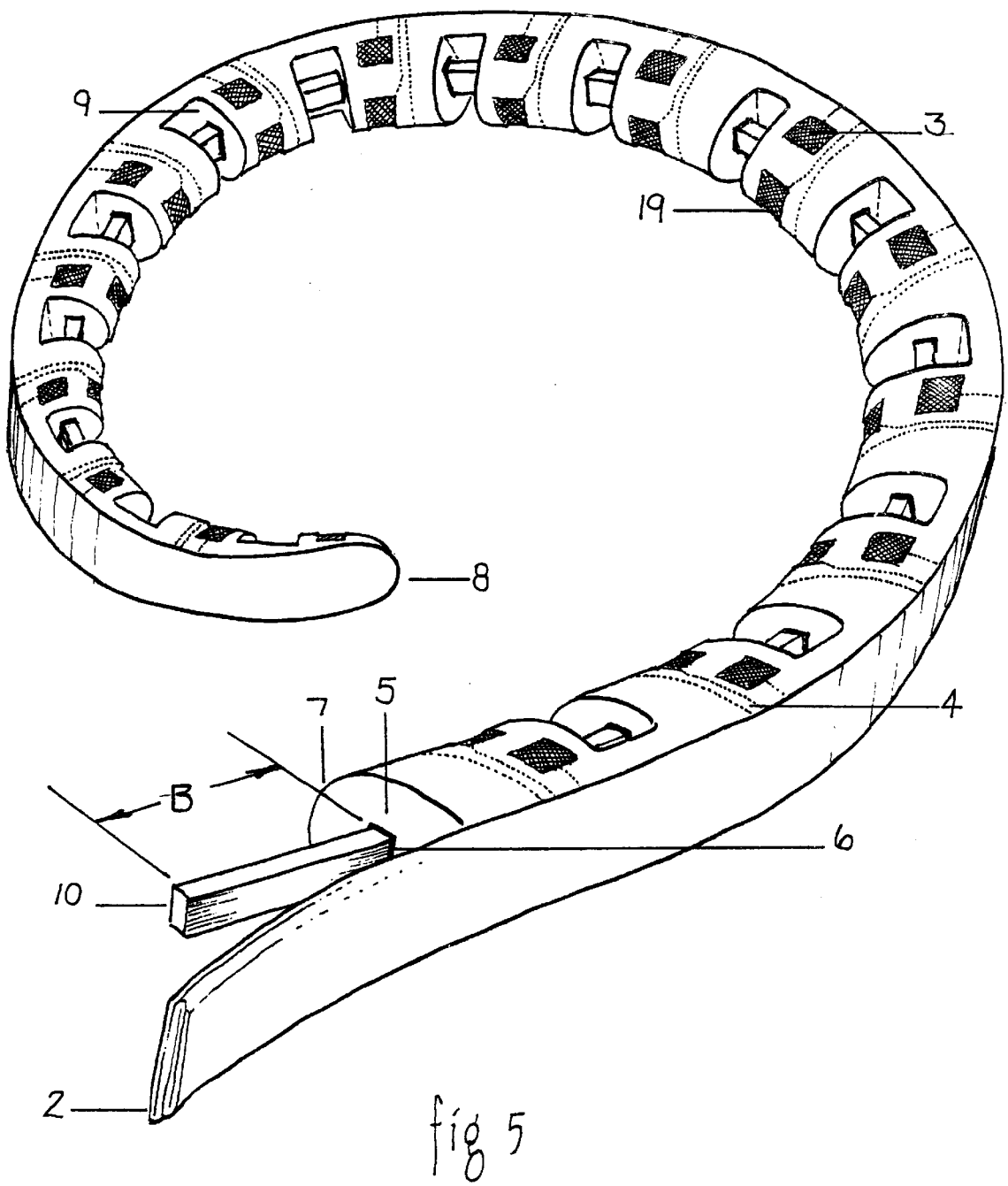
FIG. 5 is a perspective view of the preferred embodiment of the invention showing the partially uncoiled state of the conical helix-shaped electrode array with the partially circumferential notches ad-modiolar disposed.
Figure 6:
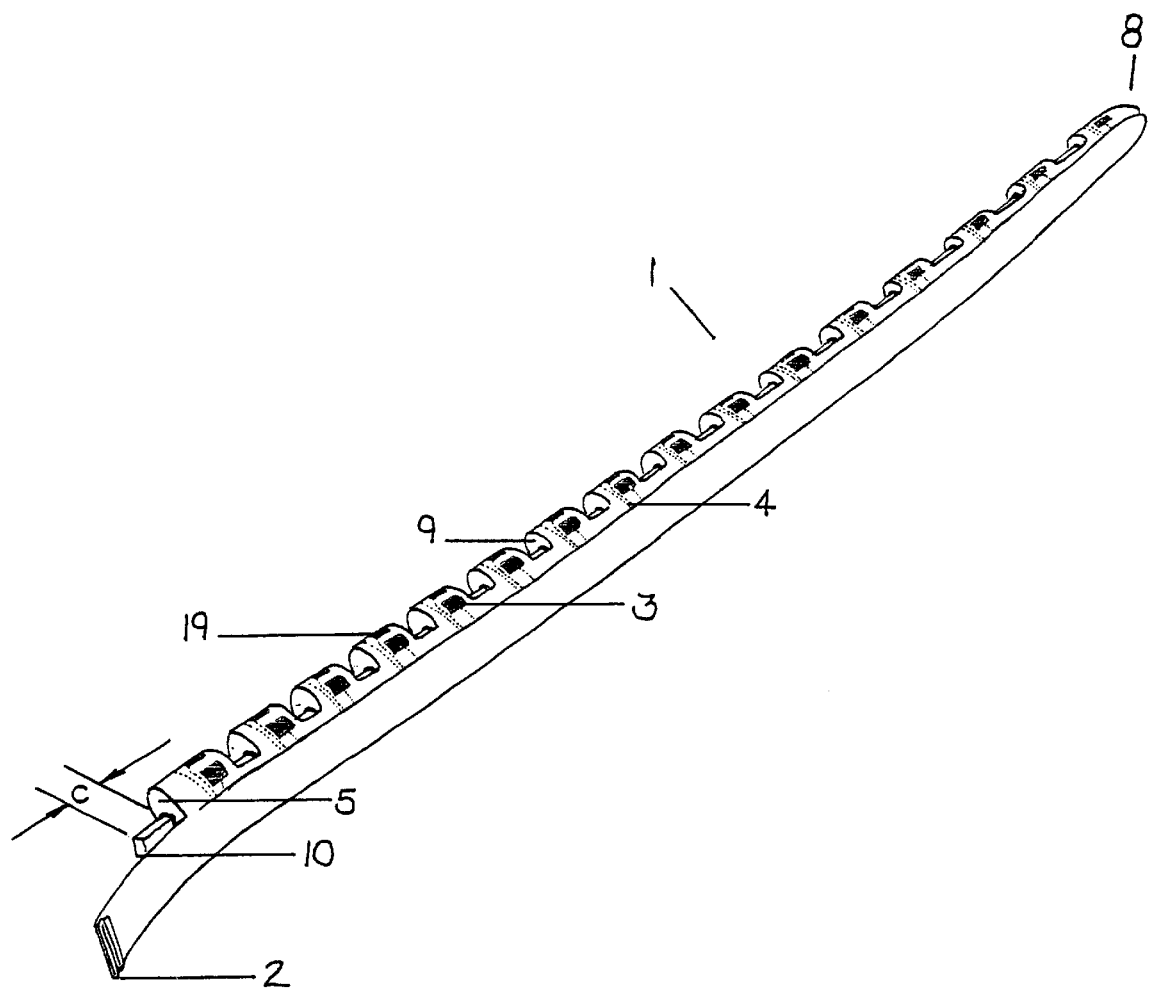
FIG. 6 is a perspective view of the preferred embodiment of the invention showing the uncoiled state of the conical helix-shaped electrode array with the notches ad-modiolar disposed.

FIGS. 4–6 illustrate the changes that can be achieved in the shape of the array as a result of gradual insertion of the beading into the carrier. The control of such shape allows the surgeon to navigate through the cochlea and selective retraction or insertion can also allow the surgeon to navigate obstructions that may be encountered upon insertion of the array.

FIG. 4 is a perspective view of the preferred embodiment of the invention showing the "normalized" relaxed state of the conical helix-shaped electrode array 1, when no external insertion or retraction force is exerted on the beading 10. The notches 9 are substantially closed.

FIG. 5 is a perspective view of the preferred embodiment of the invention 1 showing the partially uncoiled state of the three-dimensional conical helix-shaped electrode array 1, which shape can be conveniently accomplished by the surgeon pushing on beading 10 during insertion, such that the distance 'A' shown in FIG. 4 is decreased, as depicted by distance 'B' shown in FIG. 5, where 'A' is greater than 'B'. The ad-modiolar disposed partially circumferential notches 9 partially open during this uncoiling process.

FIG. 6 is a perspective view of the preferred embodiment of the invention 1 showing the substantially uncoiled state of the three-dimensional conical helix-shaped electrode array 1, which shape can be conveniently accomplished by the surgeon pushing on beading 10 during insertion, such that the distance 'C' is decreased, where distance 'B' shown in FIG. 5 is greater then distance 'C'. The ad-modiolar disposed partially circumferential notches 9 are substantially open during this uncoiled state.

The purpose of controlling the relatively coiled or uncoiled states shown in FIGS. 4 to 6 is to enable convenient and controlled electrode array insertion into the cochlea 14 (see FIG. 2), so as to minimize trauma and damage to the delicate structures within the scalae by allowing the surgeon to control, in-situ, the array flexure during insertion into the scala tympani 12, or alternately, the scala vestibuli 13.

Figure 7:
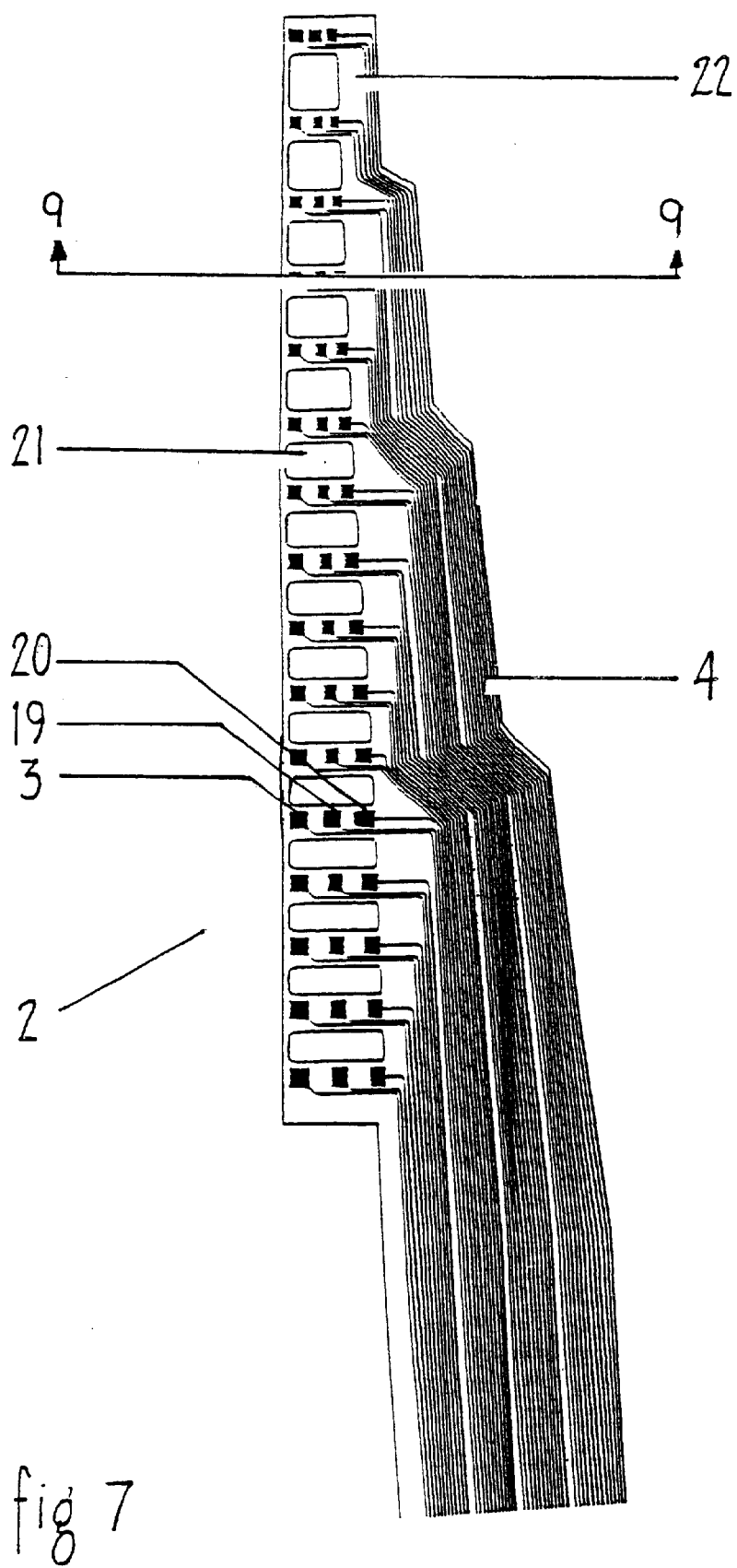
FIG. 7 is a plan view of the preferred embodiment of the invention illustrating the polymer film containing the embedded electrodes, with the embedded conductors substantially disposed all on one side of said metal electrodes.

FIG. 7 illustrates a planar view of the preferred polymer film 2 with three radially-oriented electrodes (3, 19 and 20) per group, disposed therein. Alternate embodiments include one electrode per group, two electrodes per group and four electrodes per group. Sixteen three-electrode groups are depicted in FIG. 7. Alternate embodiments include one to fifteen groups of electrodes, and more than sixteen groups of electrodes. The electrodes 3, 19, and 20 and conductors 4 can be fabricated from a biologically compatible and inert metal such as platinum, tantalum, rhodium, rhenium, iridium or alloys thereof, or a combination of two or more alloys and or metal layers thereof. The electrodes 3, 19, and 20 and conductors 4 are held in place by an inert film material 22, preferentially the polyfluorocarbon FEP, although any biologically inert, high dielectric constant flexible material would be suitable. The "cut-outs" 21 are disposed in the film between groups of electrodes 3, 19, and 20 to minimize buckling of the film material 22 when said film is rolled onto the carrier 5 and the combined carrier-film assembly subsequently formed into a conical helix (or spiral) shape. The electrode surface area has been chosen to ensure that the ratio of the actual surface area to the geometric surface area is sufficiently large to allow for a safe charge density to be passed through the electrode surface (see for example Brummer et. al., IEEE Trans. Biomed. Eng. Vol. BME-25, No. 5, pp 440–443, September 1977). For the preferred embodiment, the nominal area of the exposed electrode surface is about 0.10 mm$^2$ (approximately 300 $\mu$m by 300 $\mu$m, 300 $\mu$m diameter, or other shape) near the basal end, reducing to about 0.020 mm$^2$ (approximately 150 $\mu$m by 150 $\mu$m, 150 $\mu$m diameter, or other shape) near the apical end. In alternate embodiments, the electrodes can either be all the same size and shape, ranging in area from approximately 0.25 mm$^2$ to 0.0025 mm$^2$, or a variety of different sizes and shapes. A further embodiment incorporates electrodes of different sizes and shapes within an individual radially disposed group of electrodes. The actual surface area (or surface roughness) of the electrodes can be increased for some metals by acid etching the electrode surface while preserving the polyfluorocarbon film and carrier. The conductors 4 can be spaced relatively close together due to the high dielectric constant of the polyfluorocarbon film 22. For the preferred embodiment, platinum is used for the electrodes and conductor lines.

The platinum electrodes 3, 19, and 20 and conductor lines 4 can be conveniently formed using standard techniques such as laser cutting of platinum foil, chemical etching of platinum foil (see for example, R. P. Frankenthal, et. al., Journal of Electrochemical Society, 703(123), 1976) or alternatively, using well known photolithographic methods whereby a thin coating of platinum is vacuum deposited or sputtered through a photomask, with subsequent electroplating to increase the thickness of the platinum. For example, M. Sonn, et. al., (Medical and Biological Engineering, pp. 778–790, November 1974) and M. Sonn (A Raytheon Company Publication PB-219 466, available from the U.S. National Information Service, U.S. Department of Commerce) used, amongst other substrates, the polyfluorocarbon FEP as a substrate onto which platinum conductors and electrodes were sputtered, with the electrode and conductor patterns defined by photolithographic etching means. The array was insulated by coating with silicone. G. M. Clark, et. al., (J. of Laryngology and Otology, Vol. XC, No. 7, 1976) describe a multi-electrode ribbon-array using a thin 0.1 $\mu$m layer of RF sputtered platinum onto FEP teflon, subsequently insulated with teflon and the electrode stimulating areas exposed. H. D. Mercer, et. al. (IEEE Transaction on Biomedical Engineering, Vol. BME-25, No. 6, November 1978) give a description of a planar lithographic technique for fabrication of a microelectrode array for a cochlear prosthesis using a sputtered platinum layer with thin molybdenum and tungsten substrates. G. A. May, et. al. (IEEE Transactions on Electron Devices, Vol. ED-26, No. 12, December 1979) show an eight-channel tantalum-on-sapphire multielectrode array design using planar photolithography. C. R. Pong, et. al. (Ann. Otol. Rhinol. Largngol. 98:1989) attempted to form a standard "ring type design" electrode array by using planar photolithography to define the electrode features, RF sputtering platinum onto a polyimide substrate, rolling up the film substrate into a cylindrical shape, and filling it with silicone to provide structure. J. L. Parker et. al., in U.S. Pat. No. 5,720,099, describe a photolithographic technique for fabricating an elongated electrode array assembly by first depositing pads on a sacrificial layer, adding wires to the pads (such that the wires are self-supporting when the photoresist mask is removed), then embedding the wires and pads in an insulating material such as silicone elastomer, and finally removing the sacrificial layer. Those familiar with the art of photolithography and electrochemical deposition processes used in the microelectronics industry will appreciate that there are a number of well established technologies for forming micro patterns of metals and polymer encapsulation thereof.

Figure 8:
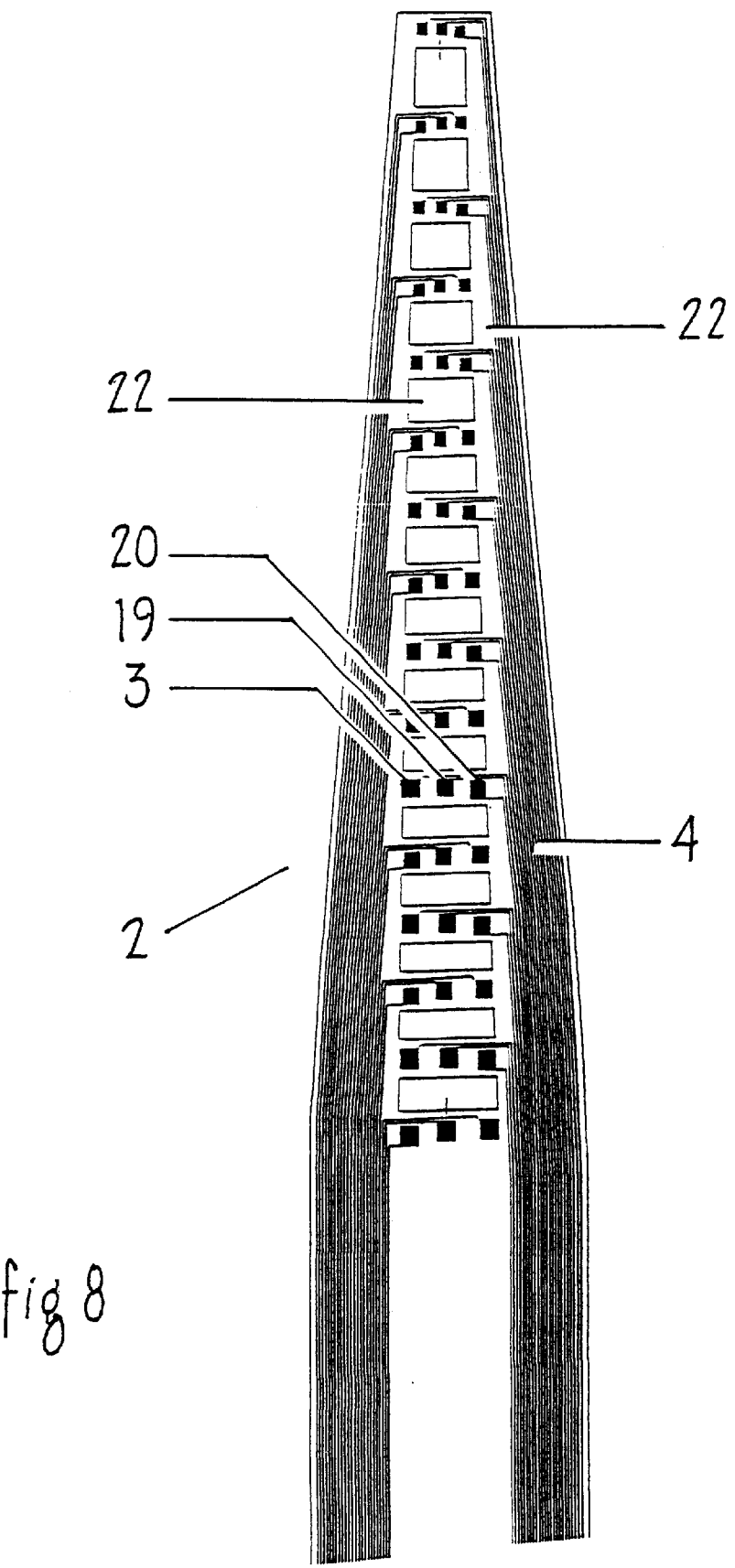
FIG. 8 is a plan view of the preferred embodiment of the invention illustrating the polymer film containing the embedded electrodes, with the embedded conductors disposed on both sides of said metal electrodes.

FIG. 8 illustrates a planar view of an alternate embodiment where the polymer film 2, containing the three radially-oriented electrodes 3, 19 and 20, has the conductor lines 4 disposed on both sides of the cut-outs 21.

Figure 9:
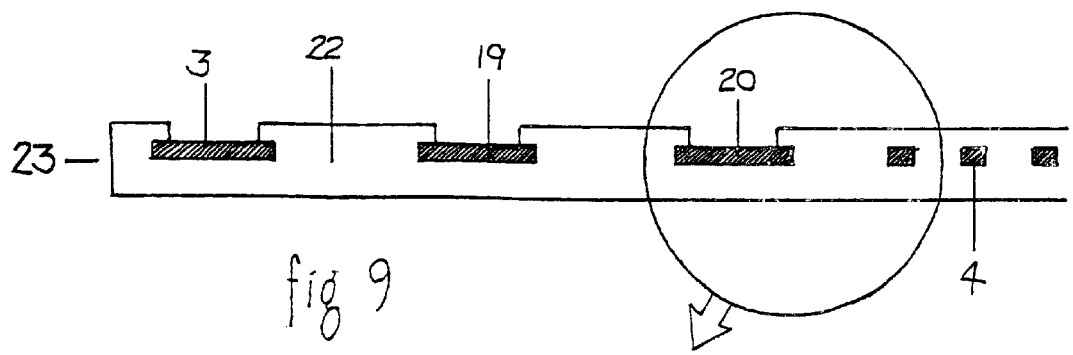
FIG. 9 is a cross-sectional view of section 'A—A' of FIG. 7 showing some embedded metal electrodes and conductors.

FIG. 9 shows a cross-sectional view 'A—A' from FIG. 7. The electrodes 3, 19, and 20 have approximate dimensions of 300 $\mu$m by 300 $\mu$m (square), by 5–50 $\mu$m (thickness) at the basal end, reducing to about 150 $\mu$m by 150 $\mu$m (square), by 5–50 $\mu$m (thickness) at the apical end. The conductors 4 have an approximate width of 10–100 $\mu$m and an approximate thickness of 5–50 $\mu$m. The thickness of the encapsulating film 23 is about 20–100 $\mu$m. The electrodes 3, 19, and 20, shown in FIG. 9, have the encapsulating film substantially removed from one side so as to expose the metal surface of said electrodes to the conducting fluid within the cochlear scala(e).

Figure 10:
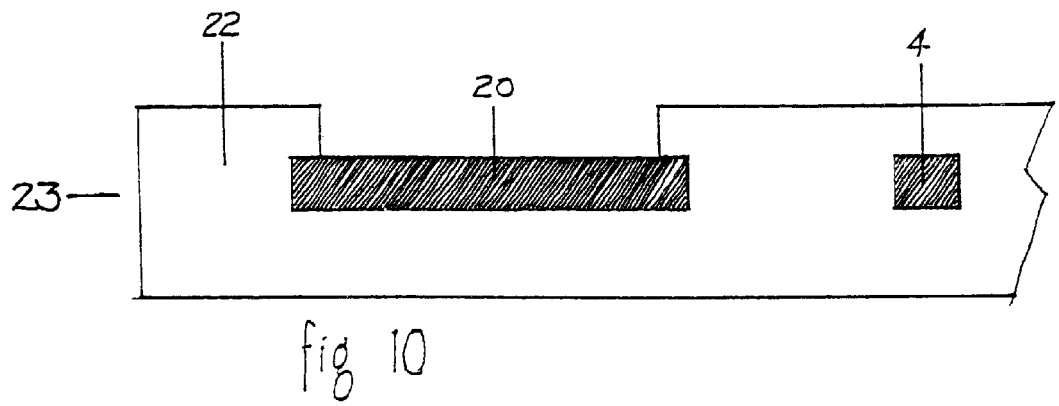
FIG. 10 is a larger scale cross-sectional view of FIG. 9 showing one metal electrode and one conductor.
Figure 11:
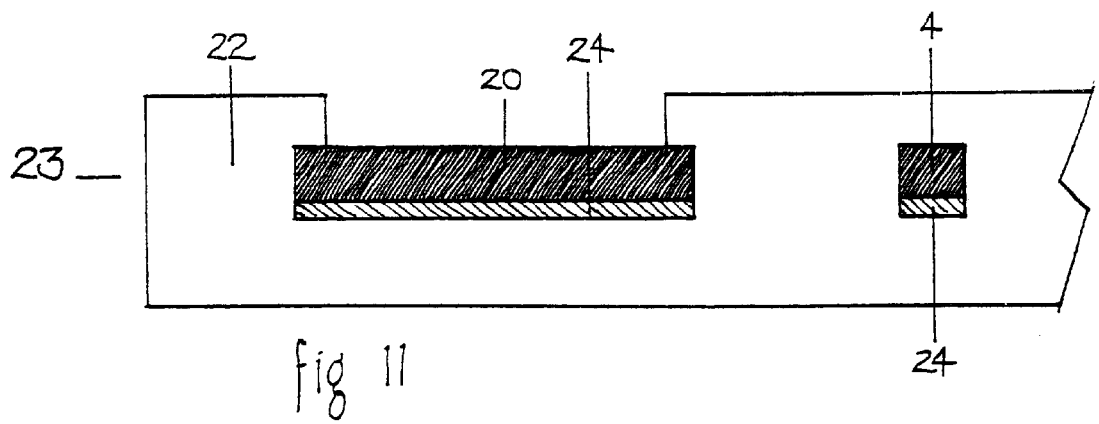
FIG. 11 is a larger scale cross-sectional view of FIG. 9 showing one metal electrode and one conductor, each having an additional substrate metal layer.
Figure 12:
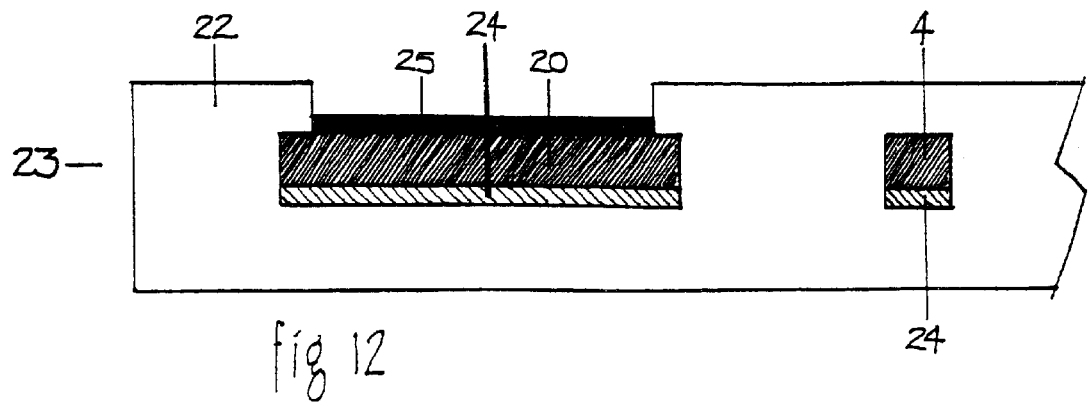
FIG. 12 is a larger scale cross-sectional view of FIG. 9 showing one metal electrode and one conductor, each having two additional metal layers, one above and one below.

FIG. 10 is an enlarged view of FIG. 9. FIG. 11 shows one alternate embodiment whereby a gold layer 24 of about 0.1 to 10 μm thickness is deposited as a first layer, under the platinum layer 20, during the fabrication process. Such a feature provides the advantages of lower electrical resistance for the conductor lines, better malleability than platinum, and simpler interconnects to the microelectronics circuitry that provide the input data to the electrodes. FIG. 12 illustrates an embodiment wherein a thin layer of, preferentially, iridium or rhodium 25, is disposed over the platinum layer 20 and the gold layer 24. The iridium or rhodium layer 25, although not as malleable as platinum, provides enhanced corrosion resistance and the possibility of using much smaller electrode surfaces without danger of exceeding the safe levels of charge density. The use of smaller electrodes will allow for a much higher density of electrodes, and the possibility of thus providing enhanced speech understanding to the implantee. Byers, et. al. in U.S. Pat. No. 4,721,551 describe one method of electroplating iridium onto a metallic microelectrode. Those skilled in the art will appreciate that there are a number of other methods, such as sputtering, whereby a thin (for example, 0.05 μm to 5 μm) layer of iridium or rhodium can be deposited onto the platinum electrode surface 3.

FIG. 13 is a perspective view of part of the invention 1 showing the film 2 being rolled over the carrier 5, with the beading 10 disposed within the carrier 5. In the preferred embodiment, the flat base of the carrier 26 can be heat bonded, for example, at location 27 to a portion of the film 2, and then the film is wrapped over the curved portion of the carrier 28, and the surface of the film 2 heat bonded to the curved surface of the carrier 28, such that the "cut-outs" in the film 21 substantially overlay the ad-modiolar disposed partially circumferential notches or "V" grooves 9 disposed along the length of the carrier 5.

Figure 14:
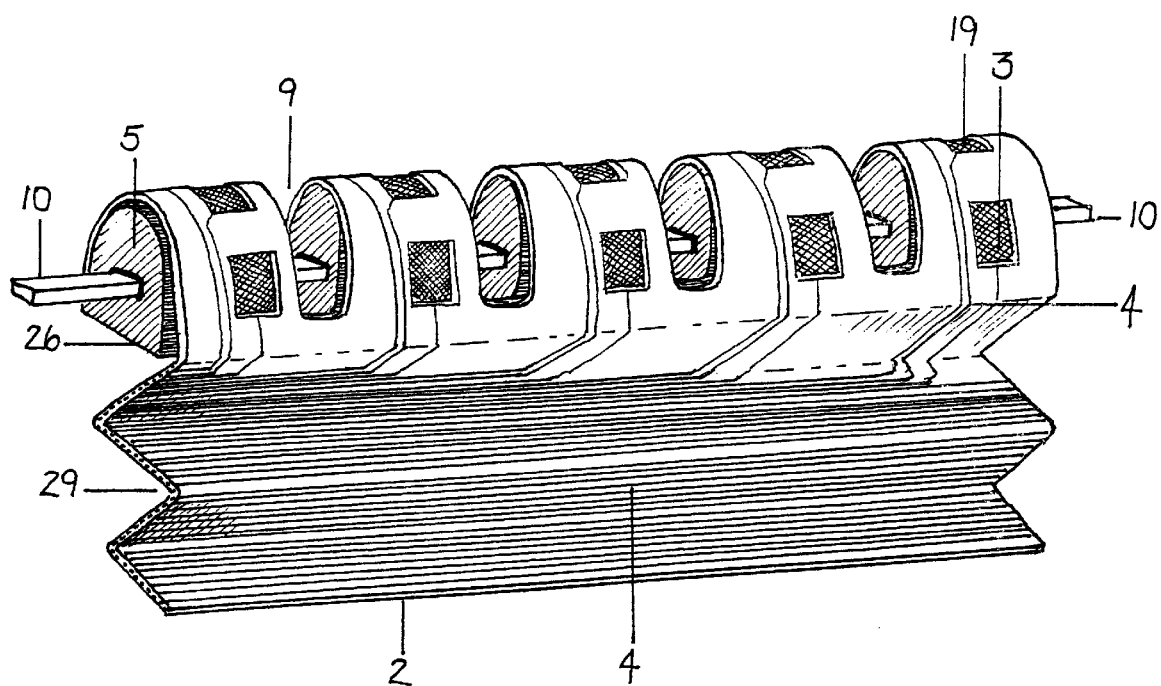
FIG. 14 is a perspective view of the preferred embodiment of the invention showing the film partially rolled over the carrier, with the beading disposed within the lumen-like hole of the carrier.

FIG. 14 shows the portion of film 2 containing the electrodes 3 and 19 bonded to the carrier 5, and the portion of film 2 containing the pleated conductors 29 ready for compression and heat bonding to the flat side of the carrier 26.

Figure 15:
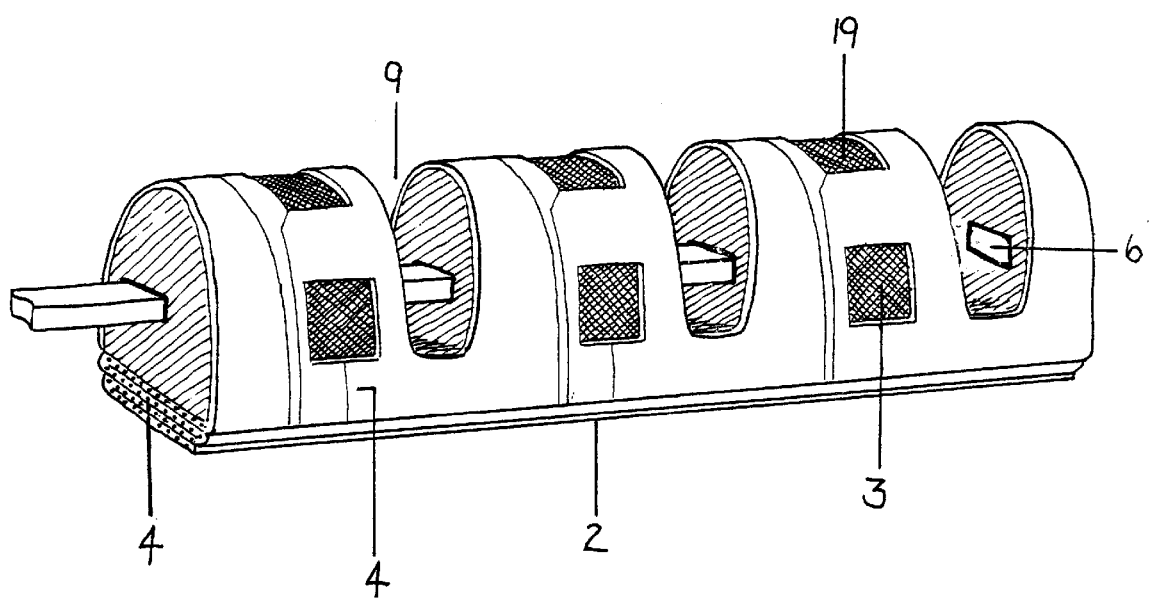
FIG. 15 is a perspective view of the preferred embodiment of the invention showing the film completely rolled over the carrier, with the conductors folded against the flat portion of the array, and with the beading disposed within the lumen-like hole of the carrier.

FIG. 15 illustrates the film 2 attached to the carrier 5 with the beading 10 partially inserted within the longitudinal hole 6 within the carrier 5.

Figure 16:
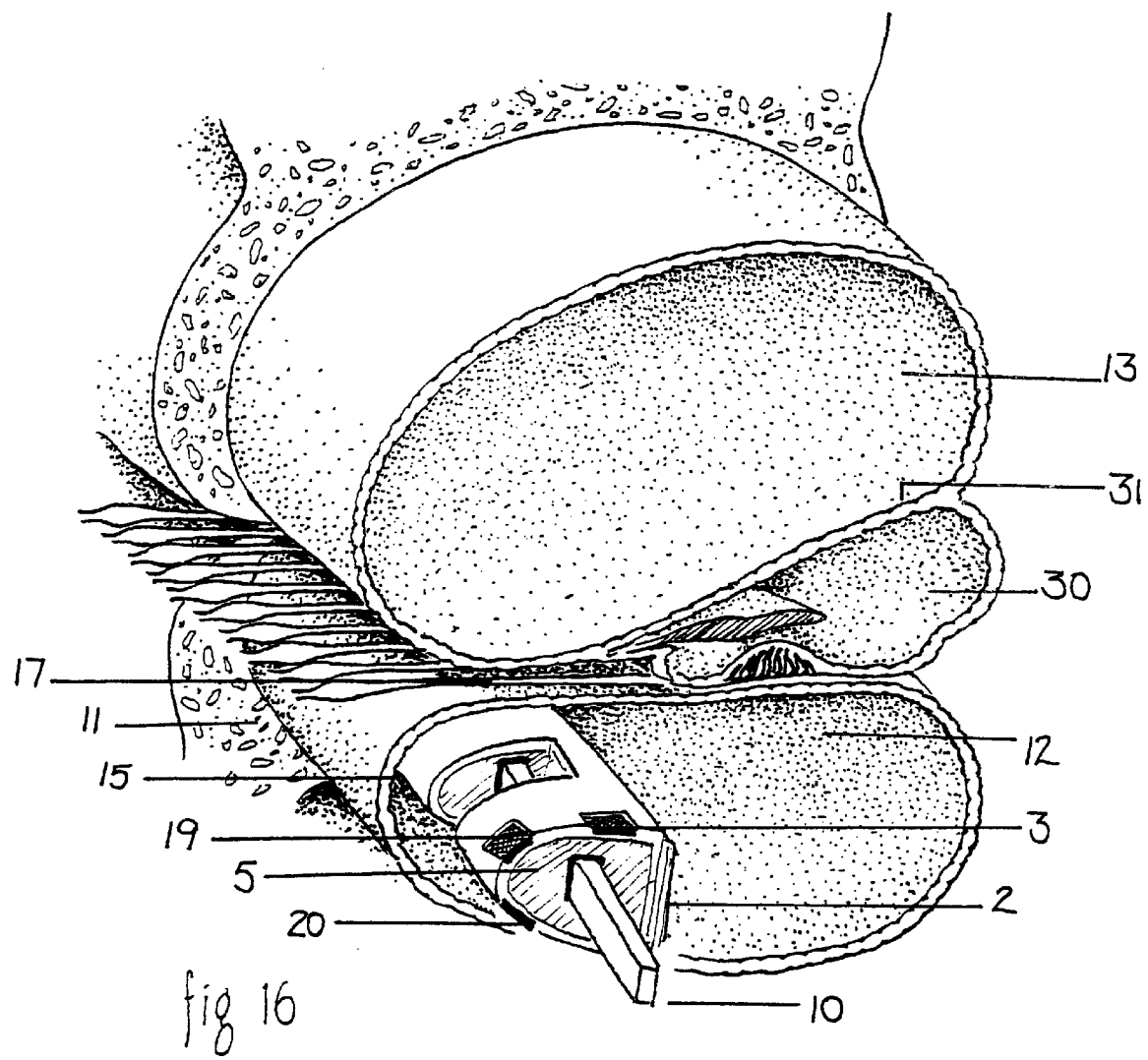
FIG. 16 is a perspective view of the preferred embodiment of the invention showing three radially-oriented electrodes disposed within the scala tympani.

FIG. 16 is a perspective view of the scalae showing a cross-sectional view of the preferred embodiment 1 disposed within the scala tympani. (Note that for discussion purposes herein, the scala media 30 is considered to be part of the scala vestibuli). The preferred embodiment is to locate the preferred embodiment 1 in the scala tympani 12, such that electrodes 3, 19, and 20 are positioned lightly against the modiolar wall 15. Such positioning will allow the electric field generated across electrodes 3 and 19, and electrodes 19 and 20, to be substantially parallel to the nerve fibers in the spiral lamina 17 and the modiolus 11, respectively. Such "neural hugging" positioning of the electrode array can be conveniently achieved by:

(a) the natural tendency of the normalized flexible conical helix (or spiral) shaped array, being slightly smaller than the scala conical helix shape, to conform to the shape of the scala, or by (b) the surgeon pulling lightly on the beading which is anchored to the apical end of the carrier, after insertion, to position the array snugly against the modiolus.

In the case where the electrode array is not shaped (ie. used in a substantially straight configuration), then the "neural-hugging" positioning can still be achieved by the surgeon pulling lightly on the beading, and anchoring said beading to maintain the resulting shape.

Since it is believed that the nerve fibers within the cochlea die back over a period of months and years, it is reasonable to expect that, for infants born deaf or persons recently deafened, electrodes 3 and 19 would provide the key electrical stimulus to the auditory nerve, since the nerve fibers in the spiral lamina 17 would still be largely stimulatable. For cases where a person has been deaf for a longer period of time, it is likely that electrodes 19 and 20 would provide the key electrical stimulus to the spiral ganglion cells in the auditory nerve. However, for some implantees, connecting electrodes 3 and 20 may give optimum results, due to their specific neural physiology. The choice of which electrodes to connect will vary amongst implantees. Such connections can be made prior to surgical insertion (ie. during device fabrication), which is simpler from an engineering perspective, but may reduce the option to achieve minimum stimulation current for some implantees. Alternatively, post-operative selection of electrode connections may be the better choice for some implantees to obtain optimum speech percepts.

Figure 17:
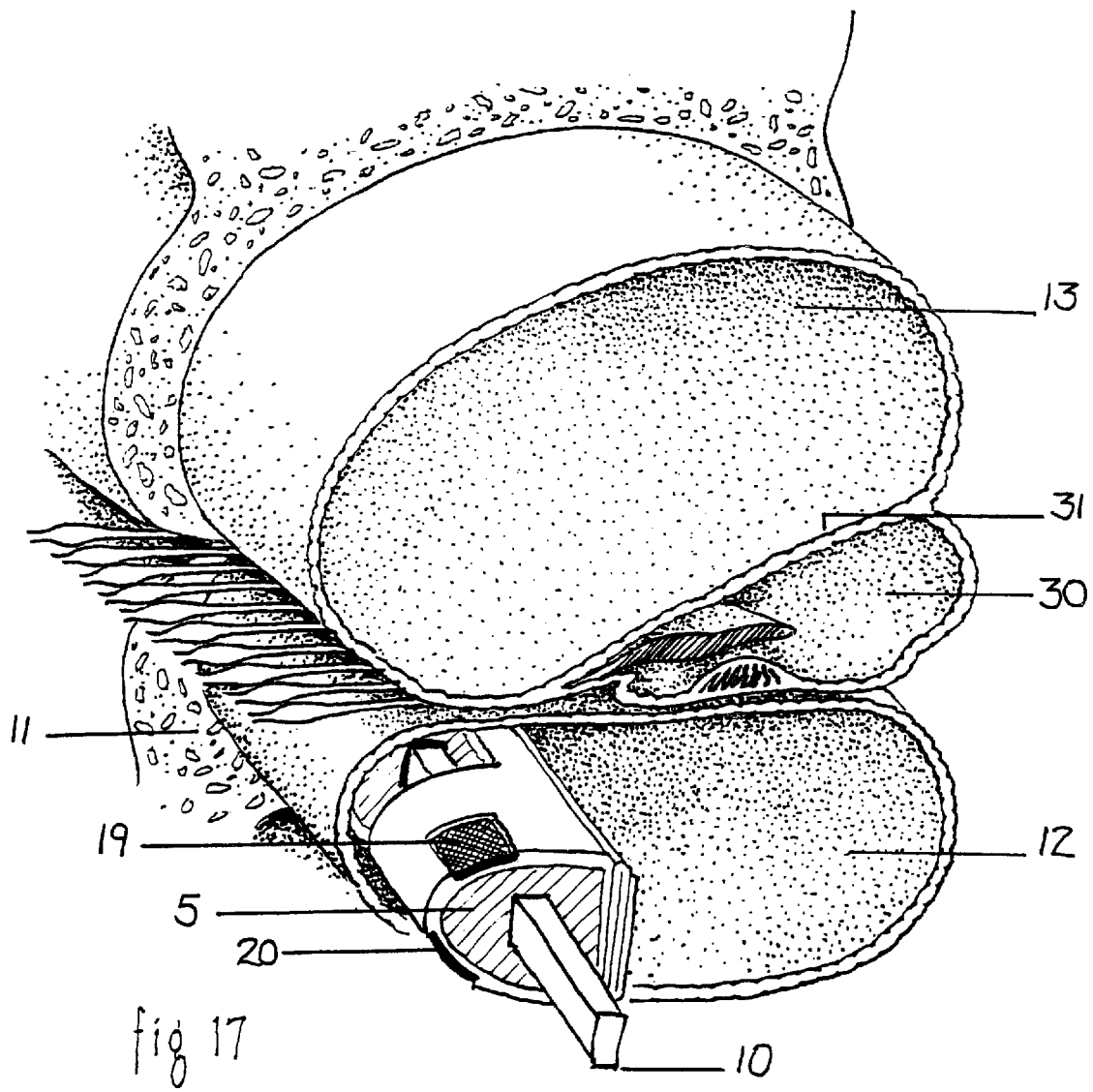
FIG. 17 is a perspective view of an alternate embodiment of the invention showing two radially-oriented electrodes disposed within the scala tympani.

FIG. 17 illustrates an alternate embodiment of the invention, where the invention is positioned as in FIG. 16, but has only two electrodes 19 and 20 per group, oriented to induce an electrical field substantially parallel to the spiral ganglia. Such a design would require simpler stimulation electronics, since only one electrode pair selection is possible.

Figure 18:
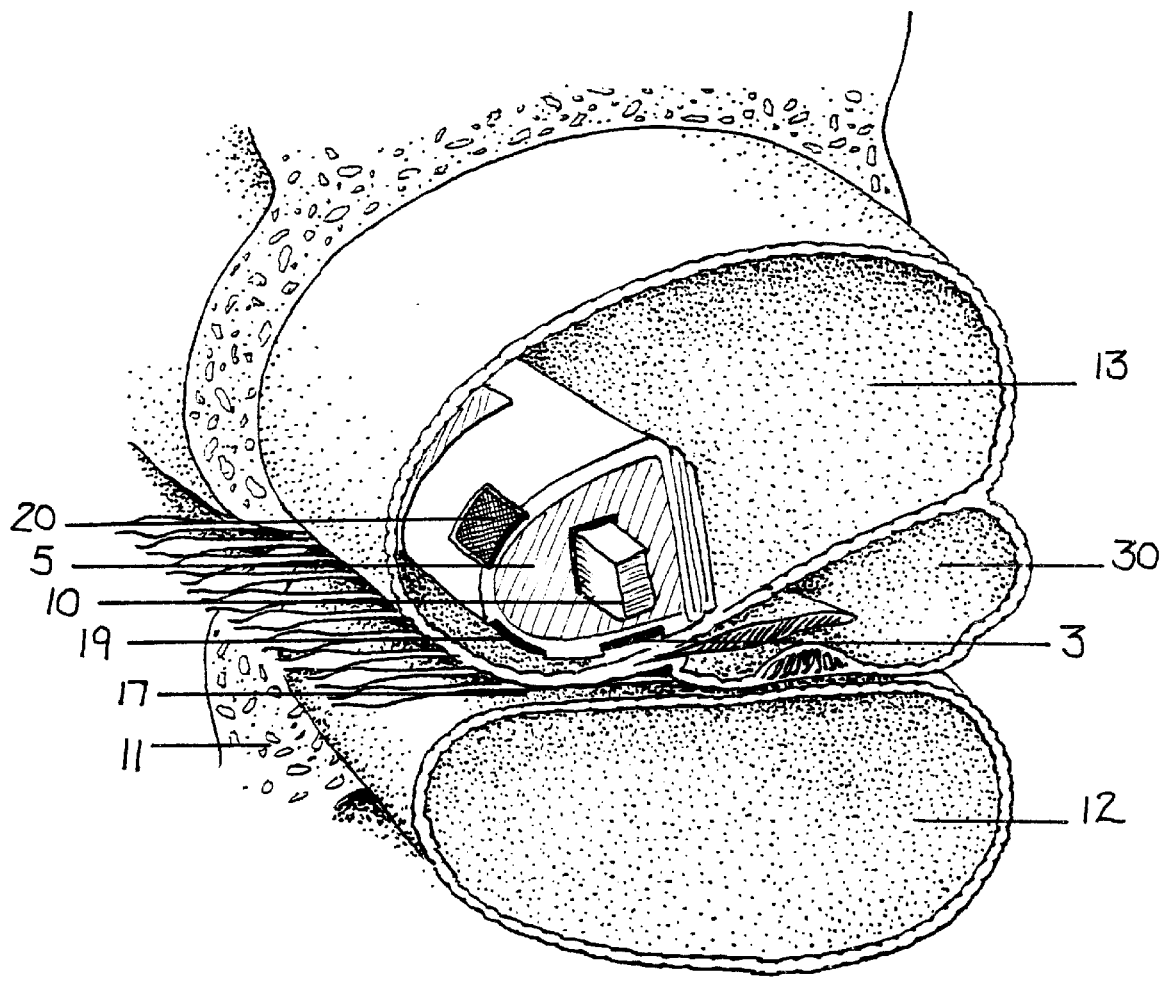
FIG. 18 is a perspective view of an alternate embodiment of the invention showing three radially-oriented electrodes disposed within the scala vestibuli.

FIG. 18 shows a further embodiment with a three electrode configuration, but inserted in the scala vestibuli 13, which may be required in cases where the scala tympani 12 is totally or partially ossified.

Figure 19:
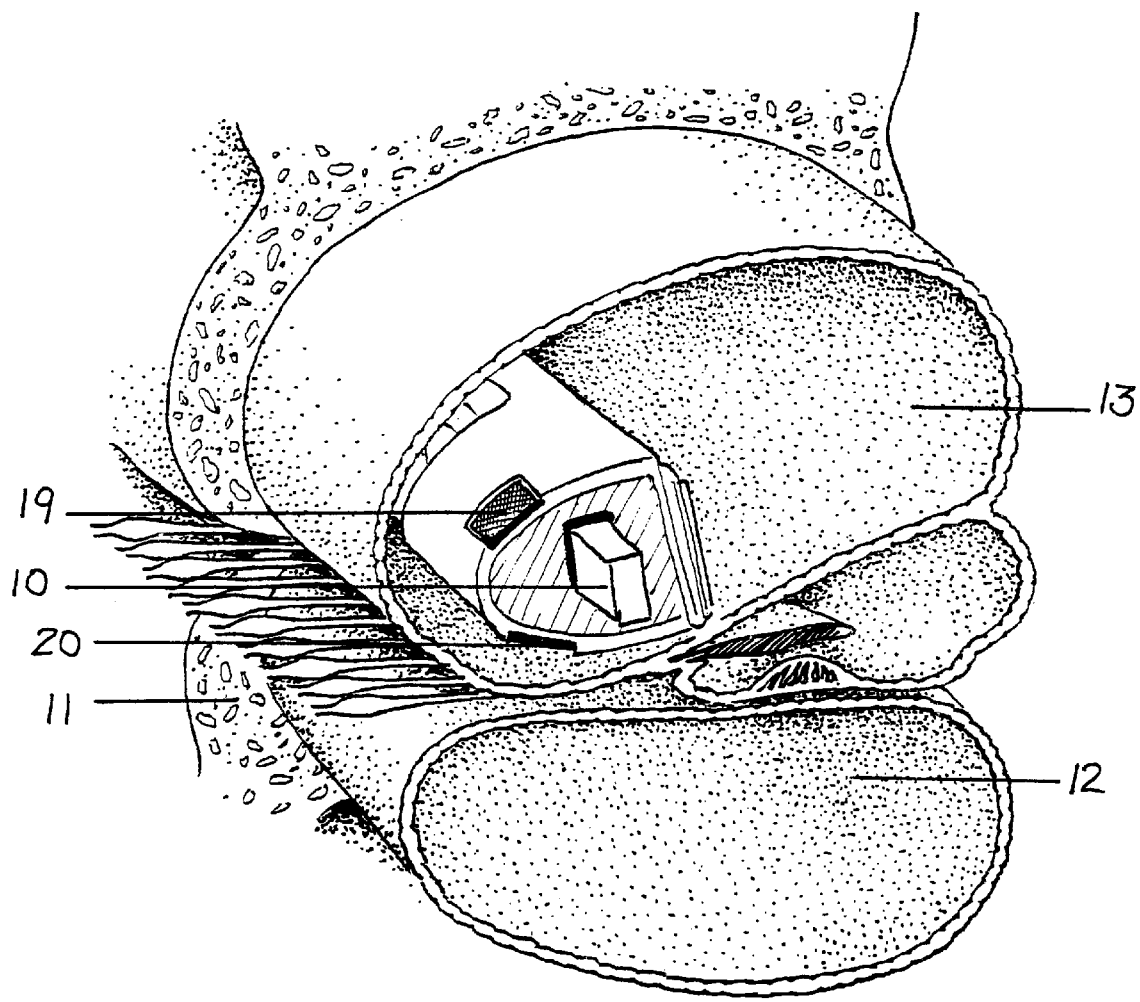
FIG. 19 is a perspective view of an alternate embodiment of the invention showing two radially-oriented electrodes disposed within the scala vestibuli.

FIG. 19 shows an alternate embodiment of the invention with two electrodes, 19 and 20, positioned in the scala vestibuli 13, which may be required in cases where the scala tympani 12 is totally or partially ossified.

Figure 20:
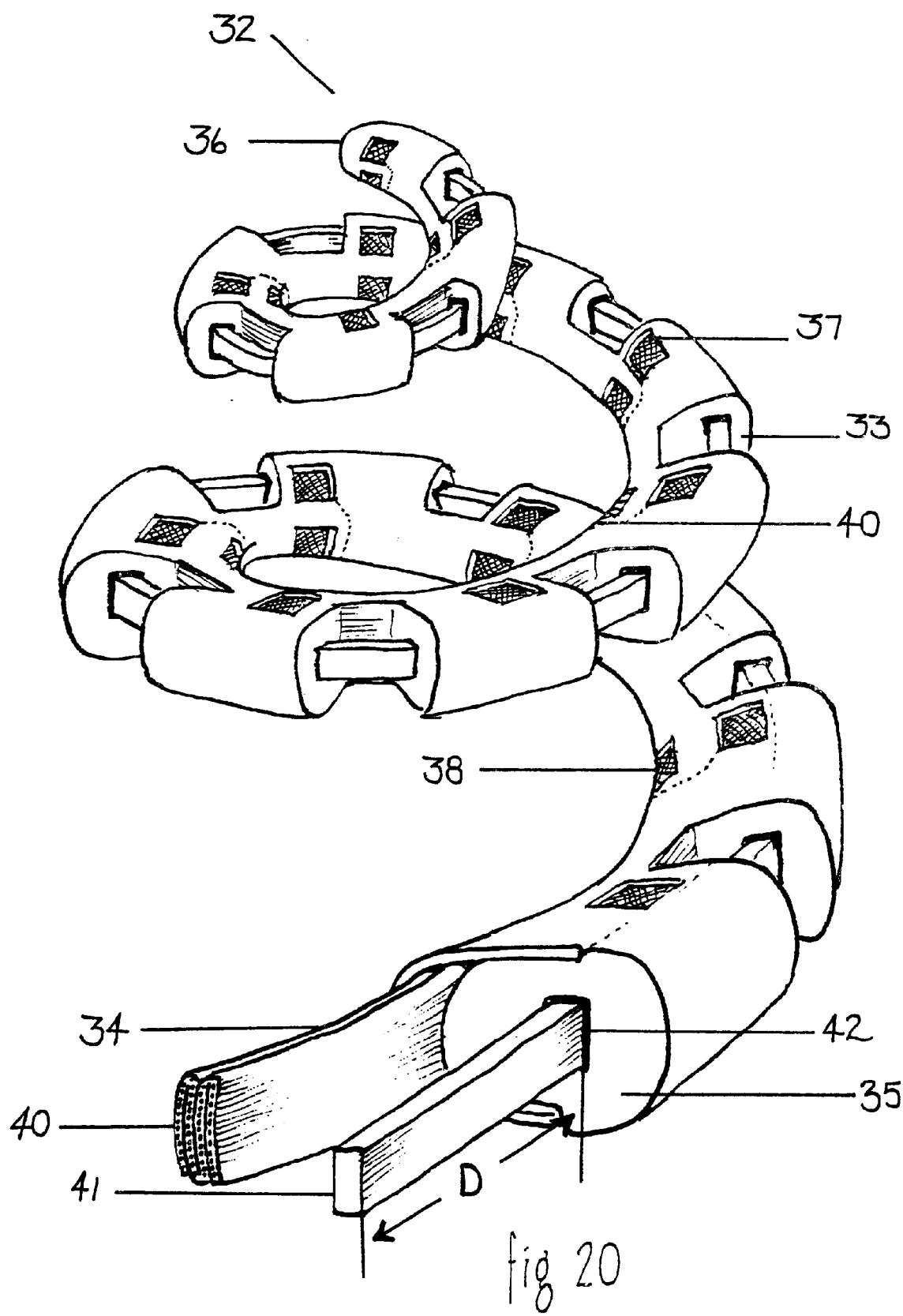
FIG. 20 is perspective view of an alternate embodiment of the invention showing the relaxed state of a conical helix-shaped electrode array, with the partially circumferential notches ex-modiolar disposed.

FIG. 20 illustrates an alternate embodiment of the invention (for the right ear) 32, where the partially circumferential notches 33 are now ex-modiolar disposed (ie. facing towards the outside of the conical helix) with the beading 41 disposed within the hole 42 of carrier 35. The carrier is attached to the film 34. The perspective view shown in FIG. 20 is for the condition where no external force is exerted on the beading 41. Whereas the notches 9 shown in FIG. 4 were closed for the relaxed state, the notches 33 shown in FIG. 20 are open for the relaxed state since the notches 33 are now ex-modiolar disposed. In a further embodiment, the beading 41 is not attached at any point within said carrier 35. The surgeon can engage the electrodes 37 and 38 against the modiolar wall by pushing on said beading 41 and anchoring substantially near the basal end of said carrier 35. An alternate embodiment is to have a two-dimensional spiral shaped electrode array with the notches 33 ex-modiolar disposed, where such a configuration is simpler to fabricate, but does not conform as ideally to the natural three-dimensional conical helix shape of the scalae during insertion or after insertion. A further embodiment is to have a straight shape when in the relaxed state (ie. not heat treated to "normalize" the shape to a conical helix or a spiral), such a device bending to the conical helix shape of the scala upon insertion. The surgeon could then push the beading, and anchor it, so as to position and hold the array substantially against the modiolar wall 15.

Figure 21:
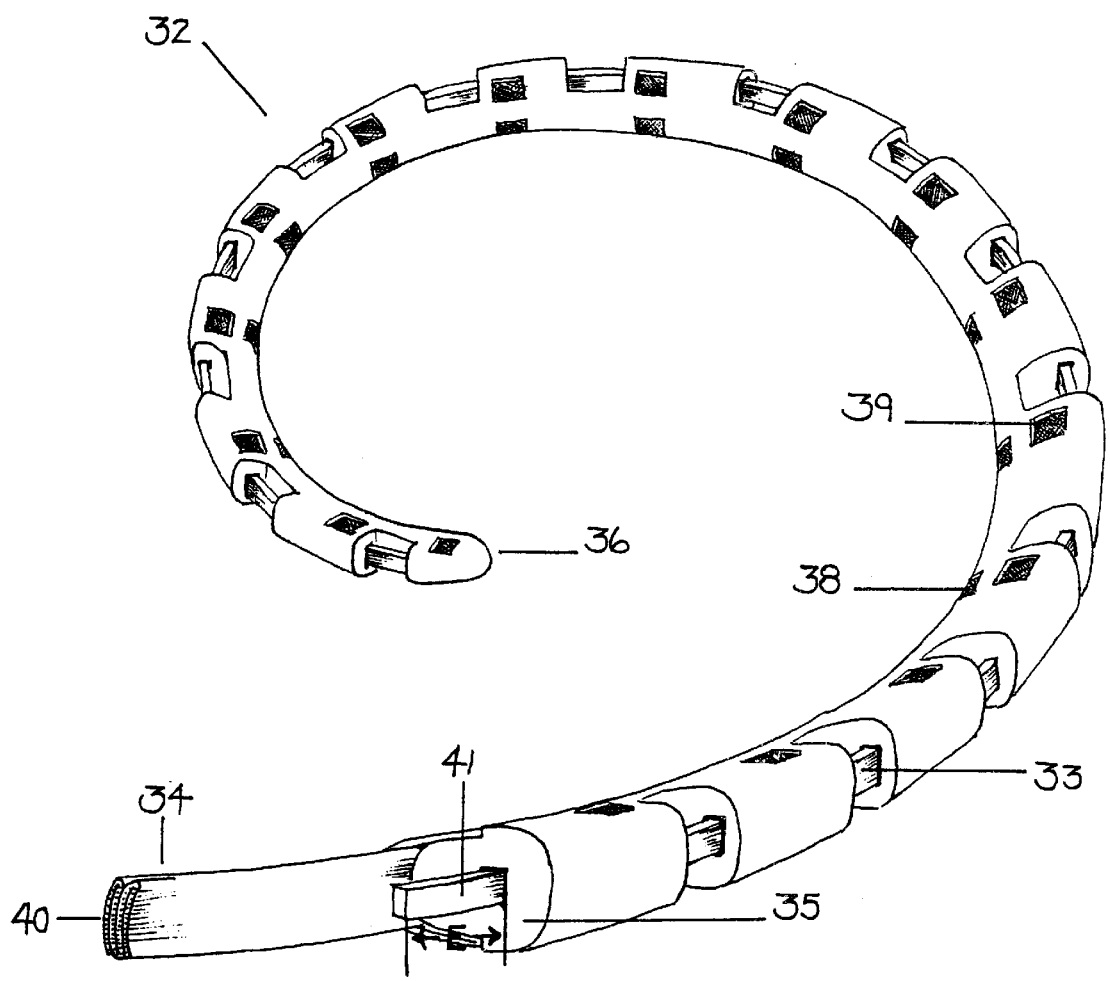
FIG. 21 is a perspective view of an alternate embodiment of the invention showing the partially uncoiled state of a conical helix-shaped electrode array, with the partially circumferential notches ex-modiolar disposed.

FIG. 21 is a perspective view of an alternate embodiment of the invention showing the partially uncoiled state of the three-dimensional conical helix-shaped electrode array 32, which shape can be conveniently accomplished by the surgeon pulling on beading 41 during insertion, such that the distance 'D' shown in FIG. 20 is increased, as depicted by distance 'E' shown in FIG. 21, where 'D' is smaller than 'E'. The ex-modiolar disposed partially circumferential notches 33 partially close during this uncoiling process.

Figure 22:
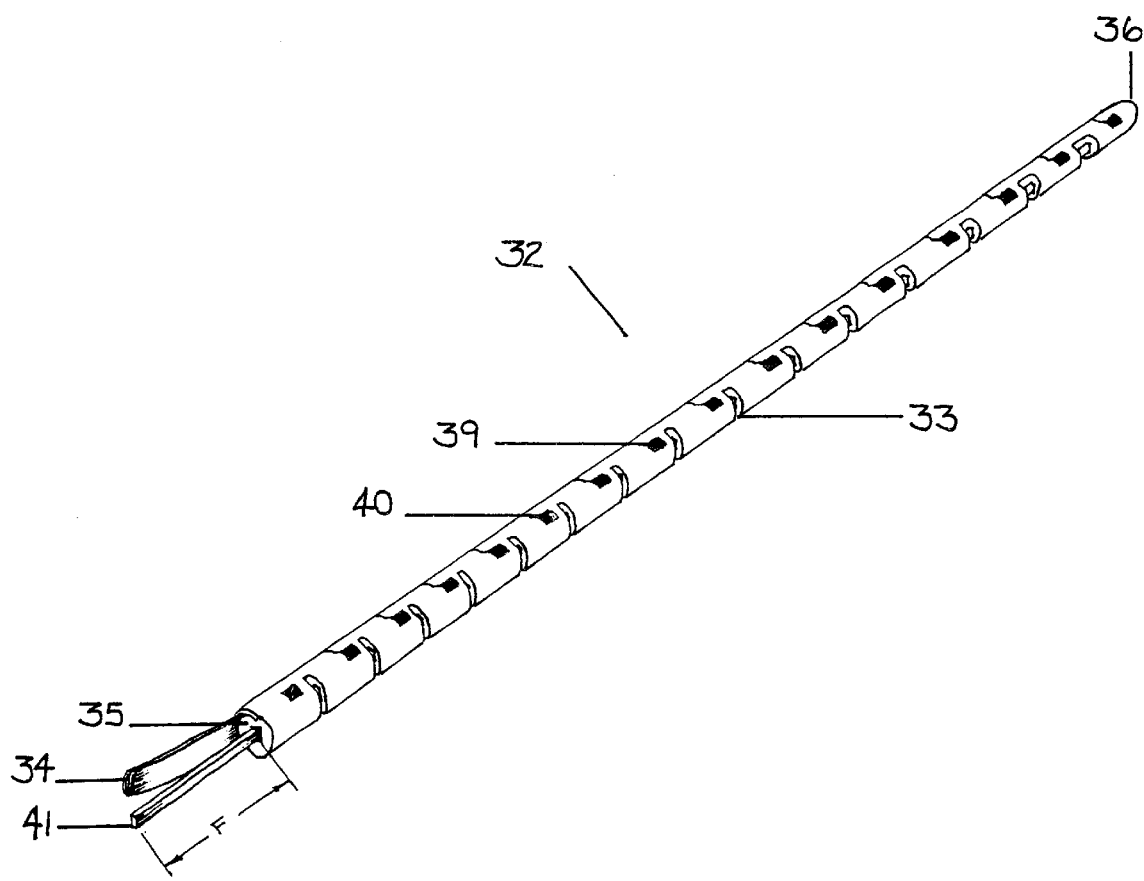
FIG. 22 is a perspective view of an alternate embodiment of the invention showing the uncoiled state of a conical helix-shaped electrode array, with the partially circumferential notches ex-modiolar disposed.

FIG. 22 is a perspective view of an alternate embodiment of the invention showing the substantially uncoiled state of the three-dimensional conical helix-shaped electrode array 32 which shape can be conveniently accomplished by the surgeon pulling on beading 41 during insertion, such that the distance 'F' is increased, where distance 'E' shown in FIG. 21 is smaller then distance 'F'. The ex-modiolar disposed partially circumferential notches 33 are substantially closed during this uncoiled state. The purpose of the uncoiled state shown in FIG. 22 is to enable convenient and controlled electrode array insertion into one of the scalae in the cochlea 14, so as to minimize trauma and damage to the delicate structures within the scalae by allowing the surgeon to control, in-situ, the array flexure during insertion into the scala tympani 12, or alternately, the scala vestibuli 13. Additionally, the tip 36 of the array 32 is rounded to further minimize damage to the scala during insertion. An alternate embodiment of the device shown in FIGS. 20–22 is to 'normalize' the array into a spiral shape that is the same or up to 50% smaller in diameter than the diameter of the conical helix shape of the human scala modiolar wall so as to position the array to "hug" the modiolar wall upon insertion. A further embodiment uses a non-normalized or partially-normalized carrier in which a normalized or memory shape beading is disposed in the lumen-like hole to give the combined carrier-beading assembly a conical helix or spiral shape after insertion.

Figure 23:
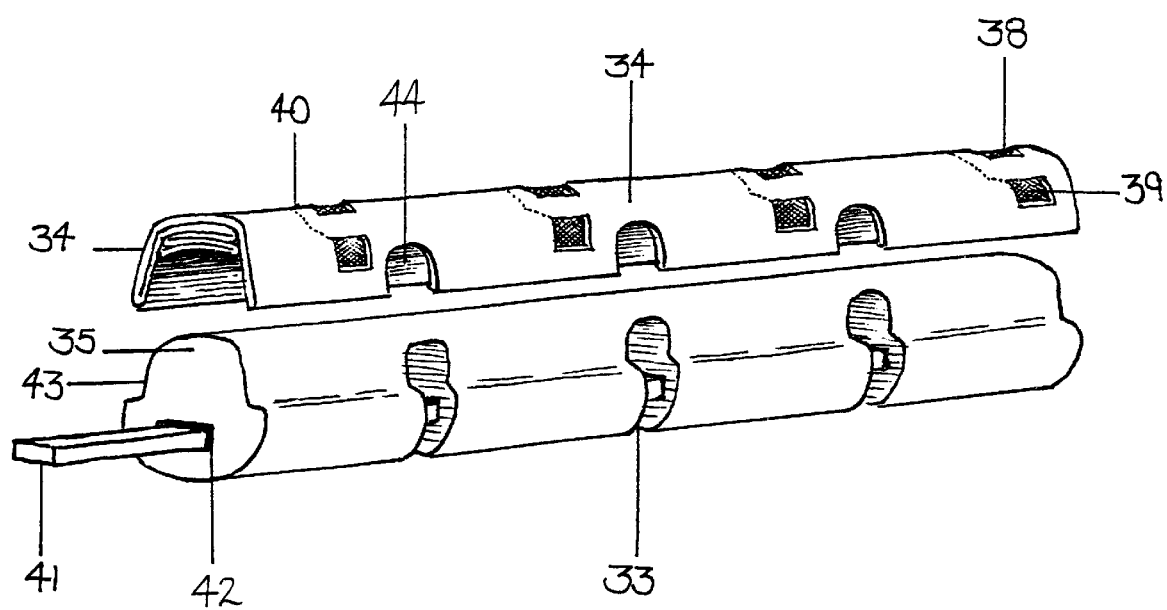
FIG. 23 is a perspective view of an alternate embodiment of the invention showing the film prior to being bonded to the carrier, with the beading positioned within the carrier hole and the partially circumferential notches ex-modiolar disposed.

FIG. 23 is a perspective view of part of an alternate embodiment of the invention showing the film 34 being rolled over the carrier 35, with the beading 41 disposed within the carrier 35. The one side of the carrier can be heat bonded, for example, at location 43 to a portion of the film 34, and then wrapped over the curved portion of the carrier, and the surface of the film 34 heat bonded to the curved surface of the carrier 35, such that the "cut-outs" in the film 44 substantially overlay the ex-modiolar disposed radially-oriented notches (or "V" grooves) 33 disposed along the length of the carrier 35.

Figure 24:
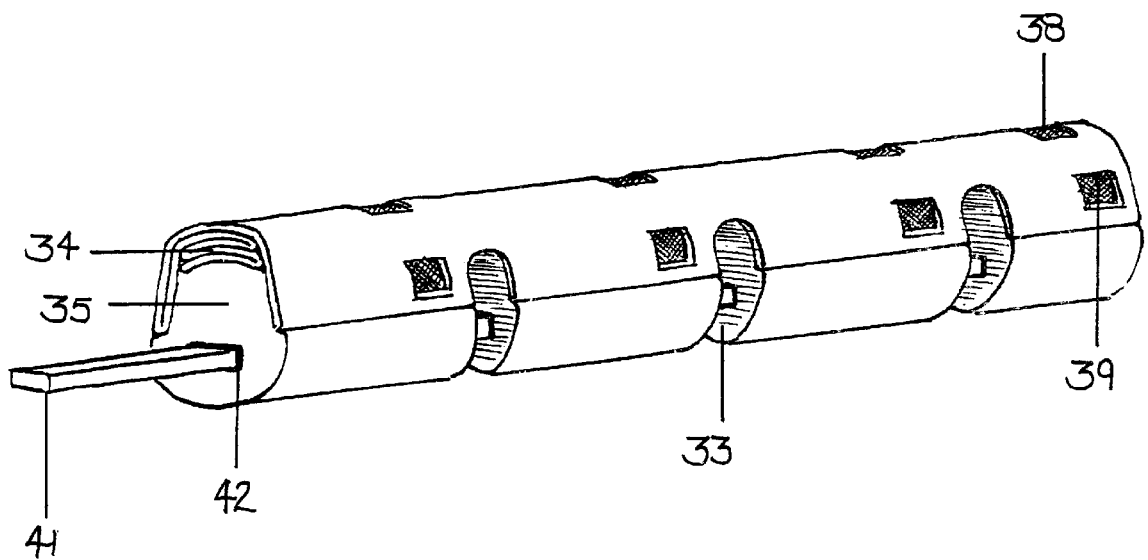
FIG. 24 is a perspective view of an alternate embodiment of the invention showing the film completely rolled over the carrier, with the conductors folded substantially against the round portion of the array, with the beading disposed within the lumen-like hole, and the notches ex-modiolar disposed.

FIG. 24 illustrates part of an alternate embodiment of the invention whereby the film 34 containing the electrodes is attached to the carrier 35 with the beading 41 partially inserted within the longitudinal hole 42 within the carrier 35, with the partially circumferential notches 33 ex-modiolar disposed.

Figure 25:
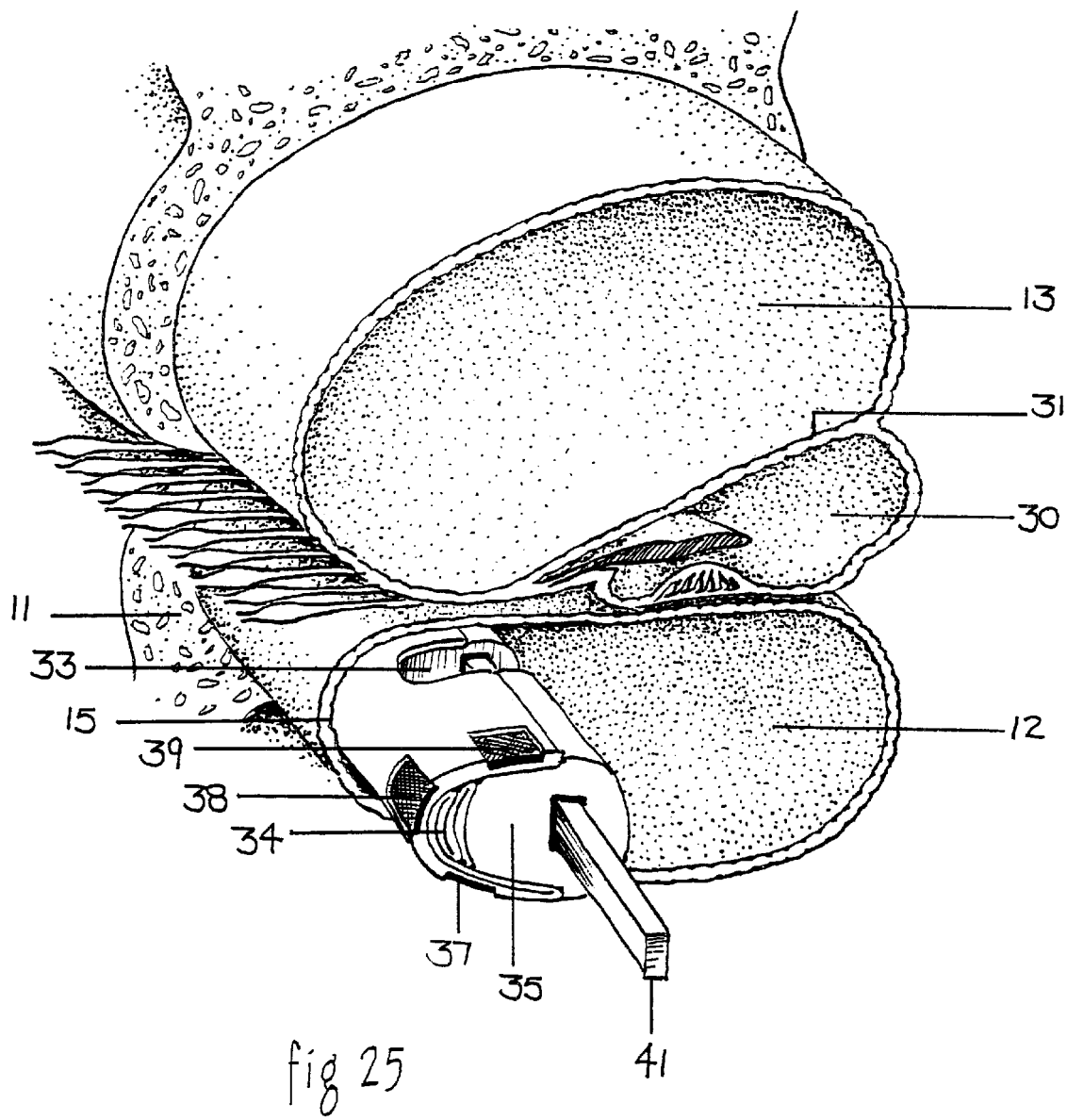
FIG. 25 is a perspective view of the alternate embodiment of the invention with partially circumferential ex-modiolar notches showing three radially-oriented electrodes disposed within the scala tympani.

FIG. 25 is a perspective view of the scalae showing a cross-sectional view of an alternate embodiment within one of the scalae. Said alternate embodiment preferentially locates the invention in the scala tympani 12, such that electrodes 38 and 39 are positioned lightly against the modiolar wall 15. Such positioning will allow the electric field generated across electrodes 38 and 39, and electrodes 37 and 38, to be substantially parallel to the nerve fibers in the spiral lamina 17 and the spiral ganglia 11, respectively. Such "neural hugging" positioning of the electrode array can be conveniently achieved by:

(a) the natural tendency of the flexible conical helix-shaped (or spiral shaped) array being slightly smaller than the scala conical helix shape and conforming to said scala shape, or by (b) the surgeon pushing lightly on the beading, after insertion, to position the array snugly against the modiolar wall 15.

In the case where the electrode array is not shaped (ie. used in a substantially straight configuration), then the "neural-hugging" positioning can still be achieved by the surgeon pushing lightly on the beading, and anchoring said beading.

Figure 26:
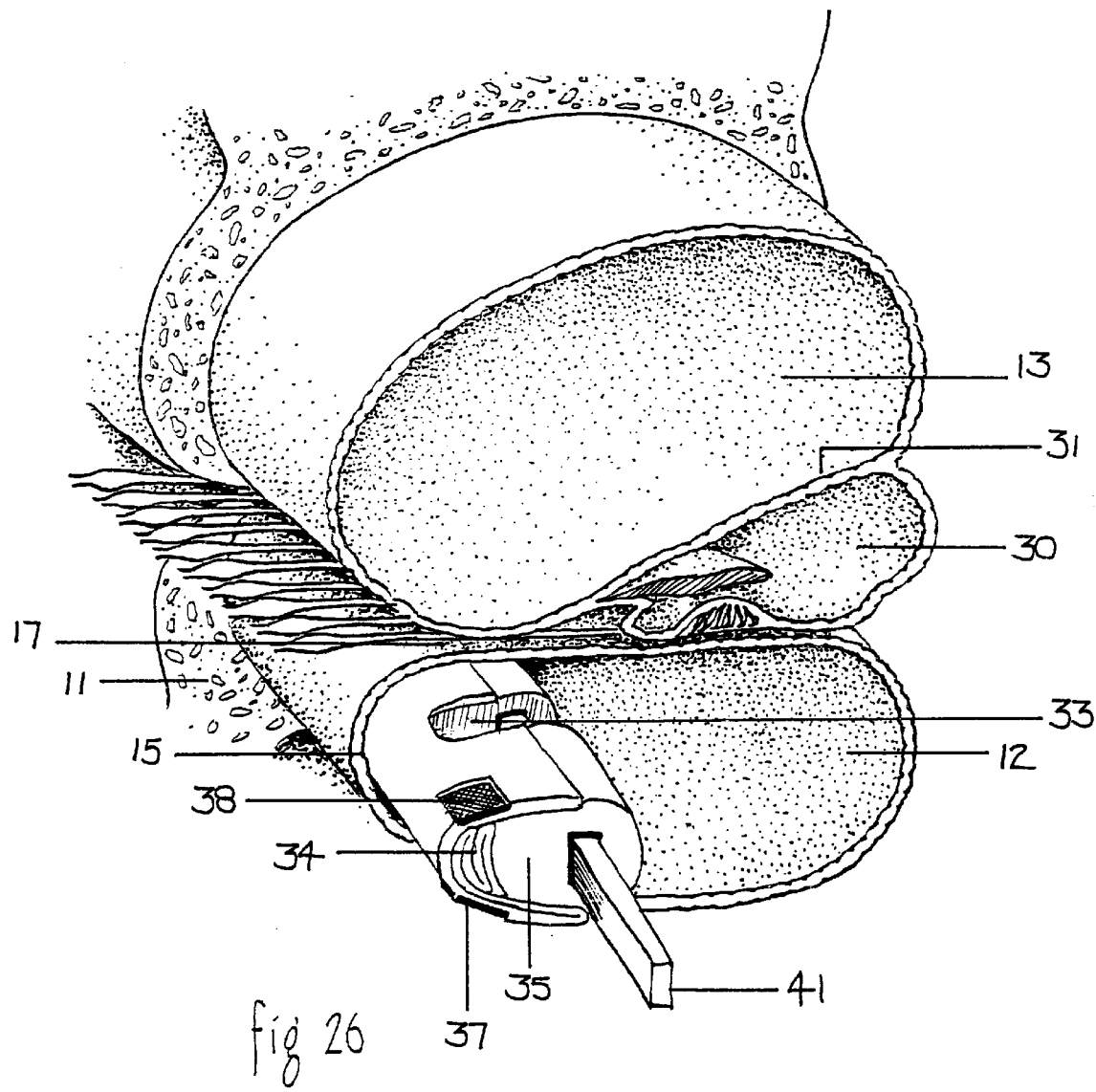
FIG. 26 is a perspective view of the alternate embodiment of the invention with partially circumferential ex-modiolar notches showing two radially-oriented electrodes disposed within the scala tympani.

FIG. 26 illustrates an alternate embodiment of the invention, where the invention is positioned as in FIG. 25, but has only two electrodes 37 and 38 per group, oriented to induce an electric field substantially parallel to the spiral ganglia 11. Such a design would require simpler stimulation electronics, since only one electrode pair selection is used.

Figure 27:
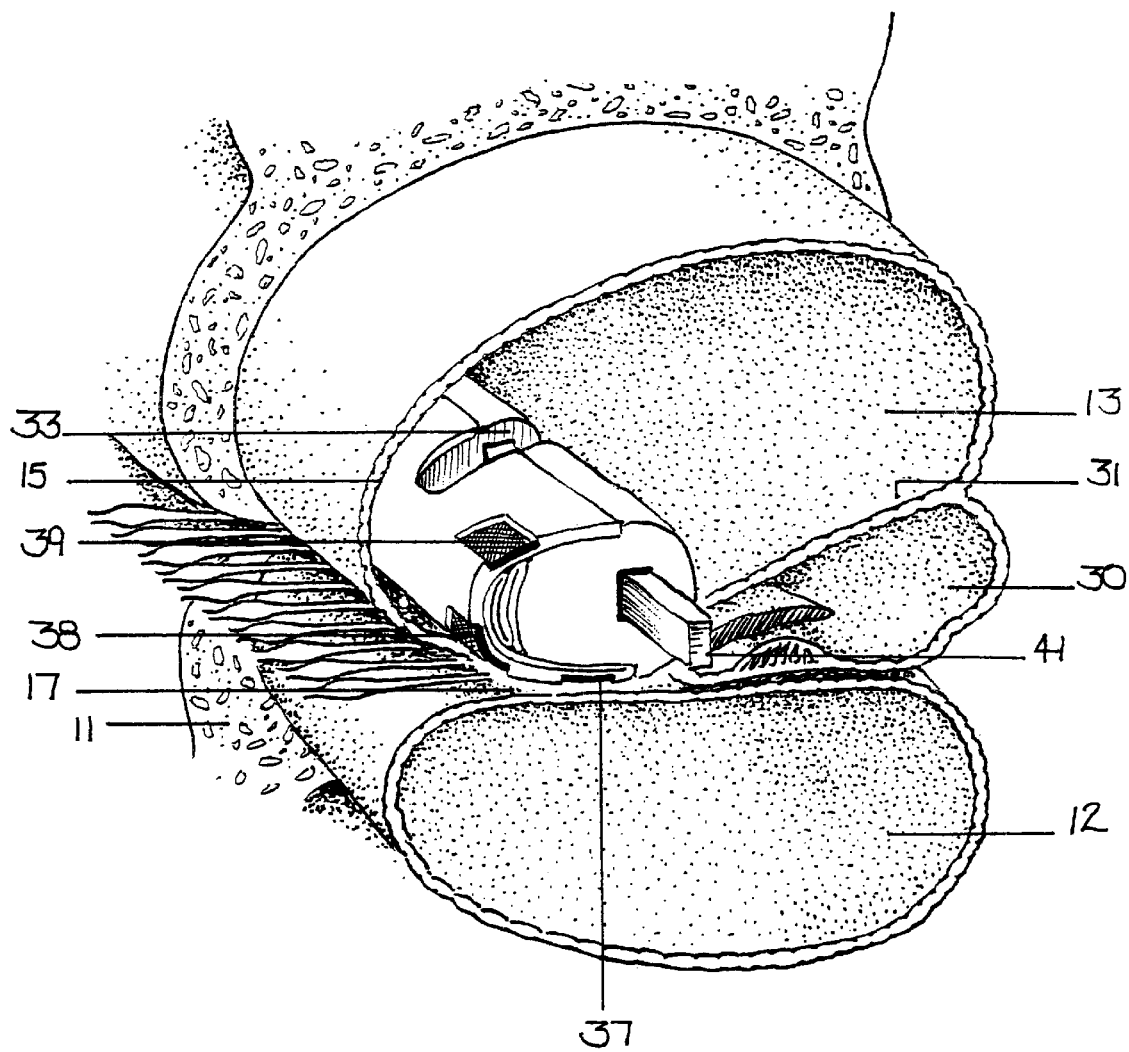
FIG. 27 is a perspective view of the alternate embodiment of the invention with partially circumferential ex-modiolar notches showing three radially-oriented electrodes disposed within the scala vestibuli.

FIG. 27 shows a further embodiment with a three electrode configuration, but inserted in the scala vestibuli 13, as may be required in cases where the scala tympani 12 is totally or partially ossified.

Figure 28:
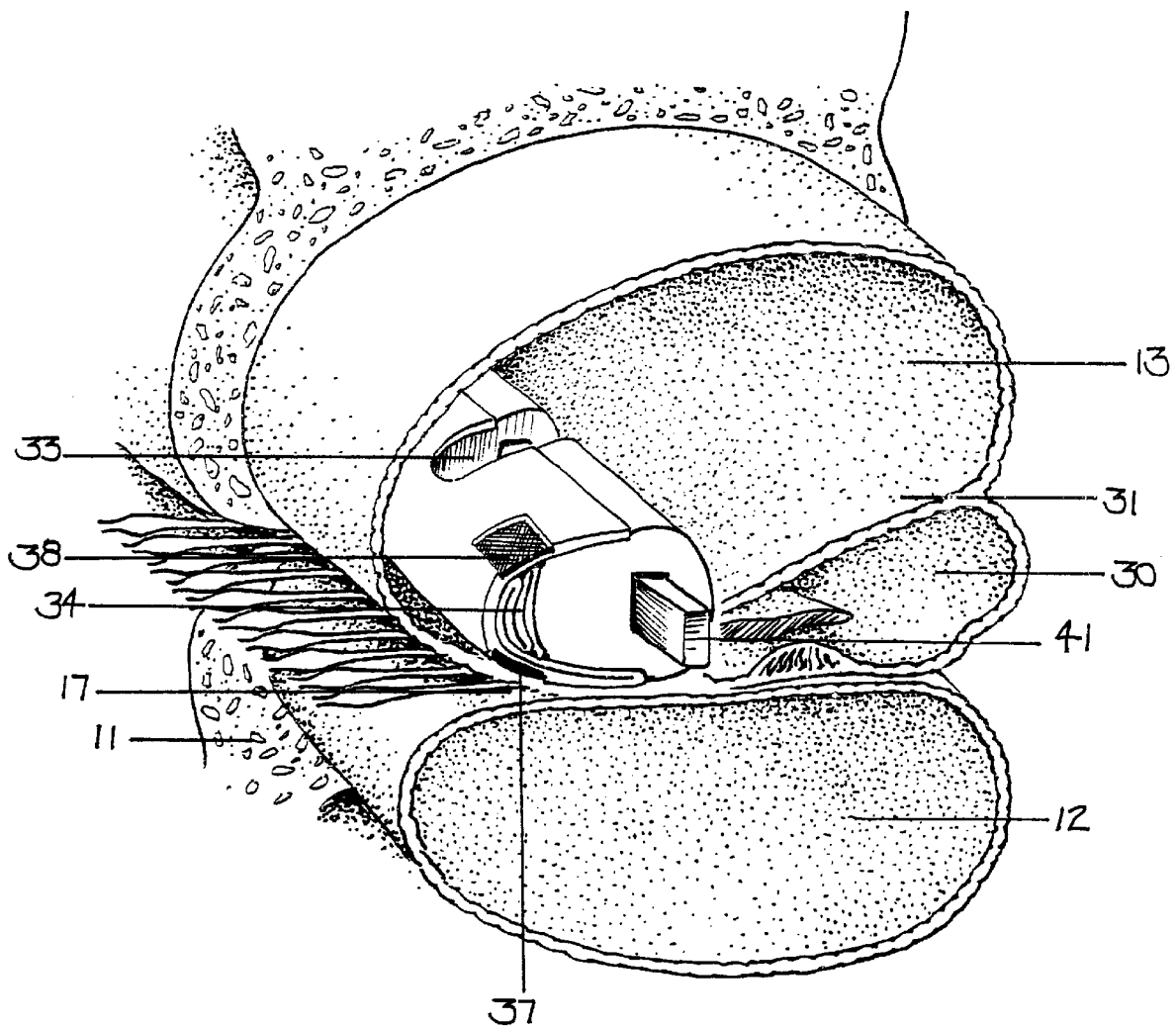
FIG. 28 is a perspective view of the alternate embodiment of the invention with partially circumferential ex-modiolar notches showing two radially-oriented electrodes disposed within the scala vestibuli.

FIG. 28 shows an alternate embodiment of the invention with electrodes 37 and 38 positioned in the scala vestibuli 13, which may be required in cases where the scala tympani 12 is totally or partially ossified.

Figure 29:
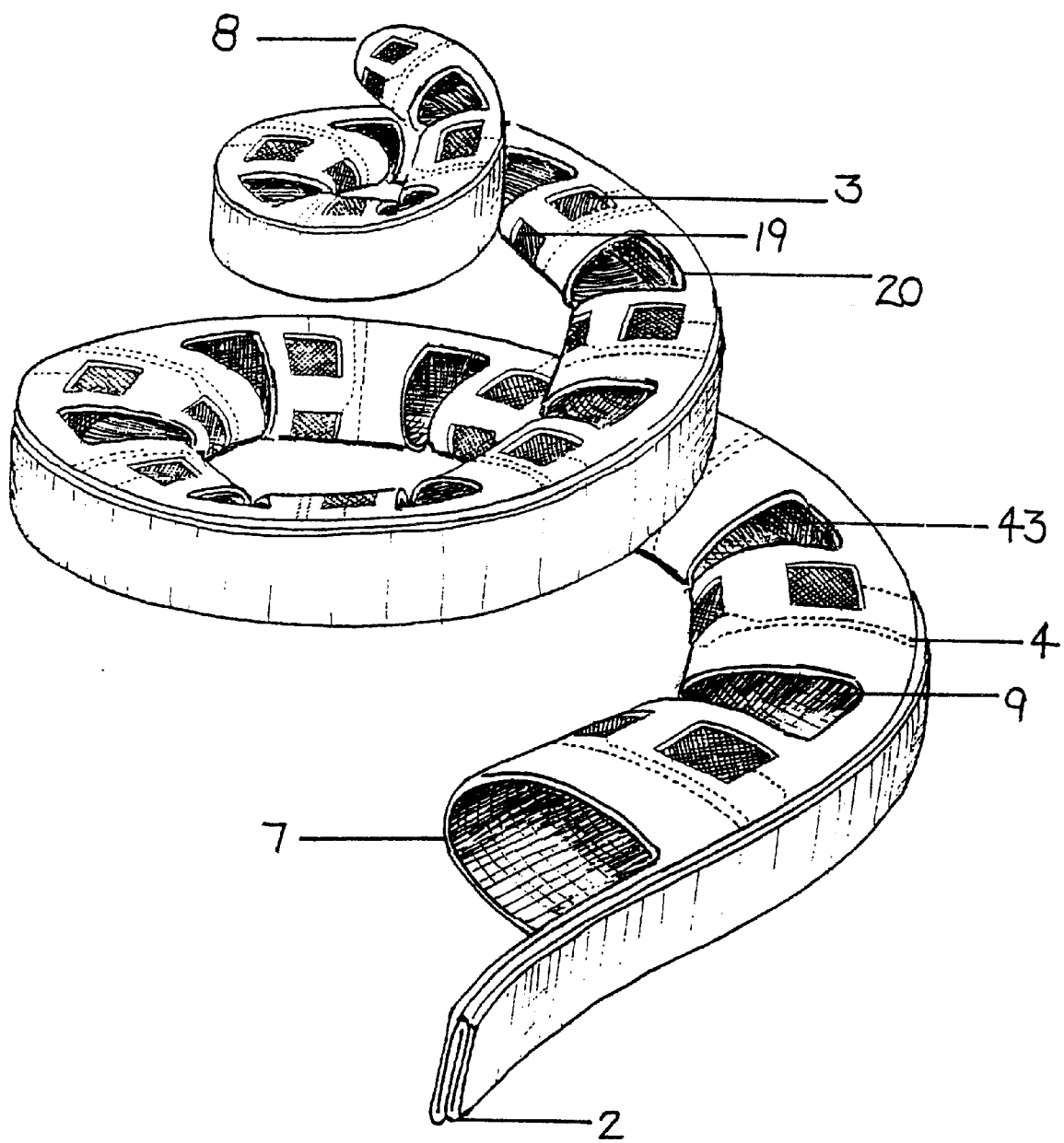
FIG. 29 is a perspective view of the alternate embodiment of the invention, comprised solely of the film containing electrodes and conductor lines, formed into a tube-like configuration in which the "cut-outs" are ad-modiolar disposed.

FIG. 29 shows a perspective view of the alternate embodiment of the invention, comprised solely of the film 2 containing electrodes 3, 19, and 20 and conductor lines 4, formed into a tube-like configuration in which the "cut-outs" 43 are ad-modiolar disposed.

Figure 30:
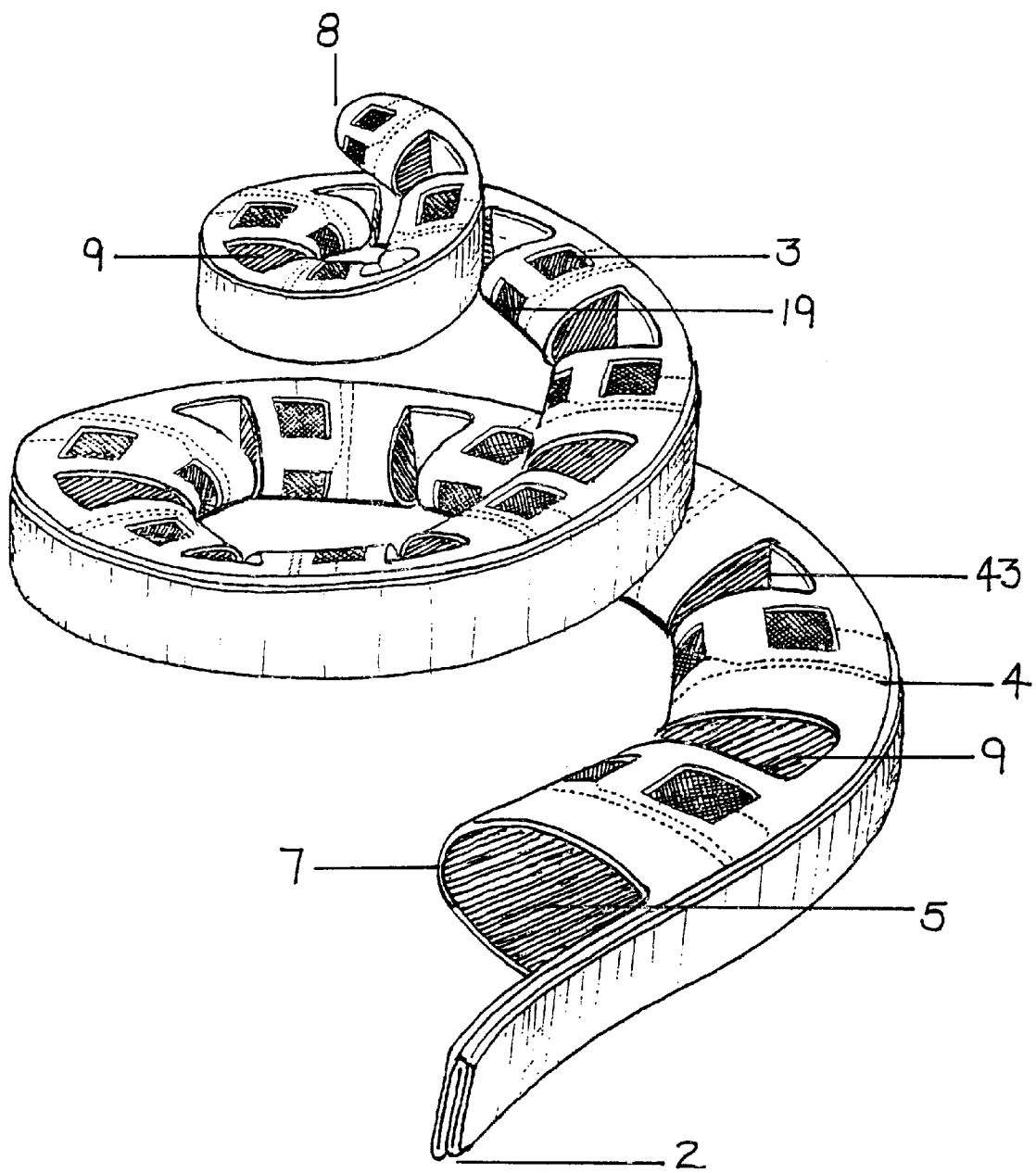
FIG. 30 is a perspective view of the alternate embodiment of the invention, comprised of the film bonded to the carrier, in which the "cut-outs" and notches (or "V" grooves) are ad-modiolar disposed.

FIG. 30 shows a perspective view of the alternate embodiment of the invention, comprised of the film 2 bonded to the carrier 5, in which the "cut-outs" 43 and notches (or "V" grooves) 9 are ad-modiolar disposed.

Although not shown, other configurations are within the scope of the invention whereby, for example, (a) an electrode array containing groups of one or four electrodes is positioned within either or both scalae, or (b) an electrode array containing groups of one, two, or three is positioned within each scala.

The above descriptions have been intended to illustrate the preferred and alternative embodiments of the invention. It will be appreciated that modifications and adaptations to such embodiments may be practiced without departing from the scope of the invention, such scope being most properly defined by reference to this specification as a whole and to the following claims.

What is claimed is:

1. A cochlear electrode array for stimulating auditory processes, comprising a bio-inert film with at least two conductor lines and at least two electrodes, said film being formed into an elongated tube-like configuration, said electrodes comprising a plurality of groups of at least two electrodes, the electrodes within each group being disposed in a substantially radial bipolar arrangement and the plurality of said groups being disposed along the longitudinal axis of said tube-like configuration.

2. The array of claim 1 wherein a plurality of cut-outs are provided in said film, each of said cut-outs being located between two groups of electrodes.

3. The array of claim 2 wherein the film is flexible but has been treated to preferentially adopt a pre-determined shape.

4. The array of claim 3 wherein said shape is a conical helix.

5. The array of claim 3 wherein said shape is a two dimensional spiral.

6. A method of fabricating the electrode array assembly of claim 1 whereby the electrodes are made of platinum and conductor lines are encapsulated between two layers of polyfluorocarbon film using a photo-lithographic process involving electroplating platinum through a photo-mask and applying first one layer of FEP film and then the other layer of FEP film using a heated vacuum press and electroplating a thin layer of irridium over the platinum, and wherein said step of electroplating a thin layer irridium is performed after the application of the first and other layer of FEP film by opening at least one layer of film to expose the electrode surfaces and performing said step of electroplating said thin layer of irridium.

7. A cochlear electrode array assembly for stimulating auditory processes, comprising an elongated bio-inert film holding at least two conductor lines and at least two electrodes, and an elongated bio-inert carrier, said film being formed into a tube-like configuration around said carrier wherein the assembly has been treated to preferentially adopt a conical helix shape.

8. A cochlear electrode array assembly for stimulating auditory processes, comprising an elongated bio-inert film holding at least two conductor lines and at least two electrodes, and an elongated bio-inert carrier, said film being formed into a tube-like configuration around said carrier and wherein a plurality of partially circumferential notches are disposed along at least a portion of the length of said carrier.

9. A cochlear electrode array assembly for stimulating auditory processes, comprising an elongated bio-inert film holding at least two conductor lines and at least two electrodes, and an elongated bio-inert carrier, said film being formed into a tube-like configuration around said carrier, and wherein at least one partially circumferential notch is provided in said carrier.

10. The assembly of claim 9 wherein a plurality of said notches are disposed along at least a portion of the length of said carrier.

11. The assembly of claim 10 wherein said electrodes are disposed along one longitudinal half of the tube-like configuration and the notches are disposed substantially along the opposite longitudinal half of the tube-like configuration.

12. The assembly of claim 10 wherein said electrodes are disposed along one longitudinal half of the tube-like configuration and the notches are disposed substantially along the same longitudinal half of the tube-like configuration.

13. The assembly of claim 9 or 10 wherein at least one end of said carrier is rounded.

14. The assembly of claim 10 wherein a plurality of cut-outs are provided in said film.

15. The assembly of claim 9 or 10 wherein said electrodes comprise a plurality of groups of electrodes, the electrodes within each group being disposed in a substantially radial bipolar arrangement on said tube.

16. The assembly of claim 9 wherein a plurality of cut-outs are disposed along the length of the tube-like configuration.

17. A cochlear electrode array assembly for stimulating auditory processes, said assembly having a generally cylindrical configuration and comprising an elongated bio-inert film holding at least two conductor lines and at least two electrodes, an elongated bio-inert carrier with a hole, and an elongated bio-inert beading adapted to slide within said hole.

18. The electrode array of claims 1 or 17 wherein the portion of the film containing only the conductors, being that portion leading away from the electrodes, is pleated to allow for lineal expansion of said conductors to accommodate cochlear and head growth.

19. The assembly of claim 17 wherein said assembly has been treated to preferentially adopt a pre-determined shape.

20. The assembly of claim 19 wherein said predetermined shape is a conical helix.

21. The assembly of claim 19 wherein said predetermined shape is a two dimensional spiral.

22. The assembly of claim 17 wherein said hole is tapered along its longitudinal extent.

23. The assembly of claim 22 wherein said hole and said beading are both tapered so that their basal ends are larger than their apical ends.

24. The assembly of claim 17 wherein said beading is attached at one end of the carrier.

25. The assembly of claim 24 wherein said end is the apical end of the carrier.

26. The assembly of claim 17 wherein said hole is offset from the longitudinal axis of said carrier.

27. The assembly of claim 17 wherein a plurality of partially circumferential notches are disposed along at least a portion of the length of said carrier.

28. The assembly of claim 27 wherein said electrodes are disposed along one longitudinal half of the assembly and the notches are disposed substantially along the opposite longitudinal half of the assembly.

29. The assembly of claim 27 wherein said electrodes are disposed along one longitudinal half of the assembly and the notches are disposed substantially along the same longitudinal half of the assembly between said electrodes.

30. The assembly of claim 29 for placement in a cochlea wherein the beading is anchored to the carrier at the basal end so as to hold it slightly in tension whereby to cause the assembly to hug the modiolar wall.

31. The assembly of claim 27 wherein a plurality of cut-outs are provided in said film.

32. The assembly of claim 31 wherein at least one of said cut-outs overlays at least one of said notches.

33. The assembly of claim 17 wherein said electrodes comprise at least one group of at least two electrodes, the electrodes within each group being disposed in a substantially radial bipolar arrangement on said assembly.

34. The assembly of claim 33 wherein a plurality of cut outs are provided in said film.

35. The assembly of claim 17 or 33 wherein said beading is attached at the apical end of said carrier.

36. The assembly of claim 17 or 33 wherein said beading is attached at the basal end of said carrier.

37. The assembly of claim 17 wherein the cross sectional shape of the beading is different from the cross sectional shape of the hole.

38. The electrode array of claim 17 wherein the film, carrier or beading is substantially comprised of a polyfluorocarbon, polyethylene, polypropylene, polyimide, polyamide, silicone, or other polymer material.

39. The assembly of claim 17 wherein at least one partially circumferential notch is provided in said carrier so as to allow the assembly to preferentially bend in a particular direction about said notch.

40. The assembly of claim 39 wherein a plurality of said notches are disposed substantially along the same longitudinal half of said assembly and a plurality of said electrodes are disposed substantially along the opposite longitudinal half of said assembly.

41. The assembly of claim 40 in place in a cochlea wherein the beading is anchored to the carrier at the basal end so as to hold it slightly in compression for causing the assembly to hug the modiolar wall.

42. The assembly of claim 17 or 39 wherein the carrier and the beading are flexible and the carrier preferentially adopts a pre-determined shape.

43. A method of positioning an electrode array according to claim 17 or 39 in a cochlea wherein the beading is withdrawn from the carrier by the surgeon after insertion.

44. A method of surgically implanting an assembly as in claim 17 or 39 wherein the surgeon selectively withdraws or inserts the beading within the carrier during insertion into the cochlea so as to cause bending or straightening of the assembly.

45. The array of claim 17 or 39 wherein said beading is memory shape wire and preferentially adopts a pre-determined shape.

* * * * *